United States Patent [19]

Sato et al.

[11] Patent Number: 5,066,575
[45] Date of Patent: Nov. 19, 1991

[54] SILVER HALIDE COLOR PHOTOGRAPHIC MATERIAL CONTAINING PYRAZOLO (1,5-B)(1,2,4)TRIAZOLE MAGENTA COUPLER

[75] Inventors: Tadahisa Sato; Osamu Takahashi; Hideaki Naruse; Yuki Mizukawa, all of Minami Ashigara, Japan

[73] Assignee: Fuji Photo Film Co., Ltd., Kanagawa, Japan

[21] Appl. No.: 473,166

[22] Filed: Jan. 31, 1990

[30] Foreign Application Priority Data

Jan. 31, 1989 [JP] Japan .................................. 1-22279

[51] Int. Cl.$^5$ ................................ G03C 1/08
[52] U.S. Cl. ................................ 430/558; 430/567; 430/571
[58] Field of Search .............. 430/558, 543, 567, 571, 430/434

[56] References Cited

U.S. PATENT DOCUMENTS

| | | |
|---|---|---|
| 4,766,057 | 3/1981 | Sakai . |
| 4,830,956 | 5/1989 | Waki ................................ 430/558 |
| 4,906,555 | 3/1990 | Hirose et al. ........................ 430/558 |
| 4,920,042 | 4/1990 | Waki ................................ 430/558 |
| 4,968,588 | 11/1990 | Ishikawa et al. .................... 430/558 |

FOREIGN PATENT DOCUMENTS

| | | |
|---|---|---|
| 0177765 | 7/1969 | European Pat. Off. . |
| 0275257 | 5/1986 | Japan ................................ 430/558 |

OTHER PUBLICATIONS

Chemical Abstracts, vol. 109, No. 13, Sep. 26, 1988, p. 623, Abstract No. 119522f.

*Primary Examiner*—Charles L. Bowers, Jr.
*Assistant Examiner*—Thomas R. Neville
*Attorney, Agent, or Firm*—Birch, Stewart, Kolasch & Birch

[57] ABSTRACT

The present invention relates to a silver halide color photographic material comprising a support having thereon at least one silver halide emulsion layer, which contains at least one nondiffusible pyrazolo(1,5-b)(1,2,4)triazole magenta coupler represented by the following general formula (I) in at least one of the silver halide emulsion layers in order to acquire high color formability and to produce a dye image excellent in hue:

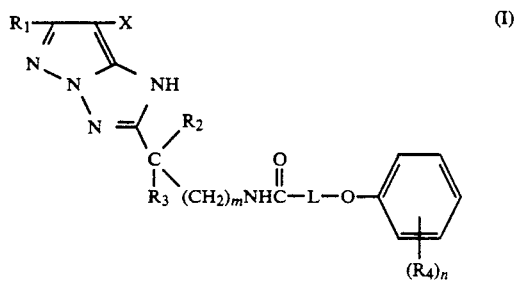

(I)

wherein $R_1$ represents an alkyl group; $R_2$ and $R_3$ each represents a hydrogen atom or an alkyl group, provided that both are not a hydrogen atom; $R_4$ represents an alkyl group, an alkoxy group or a halogen atom; L represents an alkylene group; m represents an integer of 0 to 5; n represents an integer of 0 to 5, and when n is 2 or more, the $R_4$'s may be different from one another; and X represents a halogen atom.

13 Claims, No Drawings

SILVER HALIDE COLOR PHOTOGRAPHIC MATERIAL CONTAINING PYRAZOLO (1,5-B)(1,2,4)TRIAZOLE MAGENTA COUPLER

FIELD OF THE INVENTION

The present invention relates to a silver halide color photographic material and, more particularly, to a silver halide color photographic material in which a pyrazolo(1,5-b)(1,2,4)triazole magenta coupler having high color formability and desirable hue is used to ensure excellent color reproducibility.

BACKGROUND OF THE INVENTION

It is well known that color images are formed by oxidizing an aromatic primary amine color developing agent using exposed silver halide as an oxidizing agent, and making the oxidized color developing agent react with couplers.

Most of the magenta color-forming couplers which have been widely used in practice and which have received further study are 5-pyrazolone couplers. However, it is also known that the dyes formed from 5-pyrazolone couplers have an undesirable absorption in the vicinity of 430 nm, or a yellow component, which is responsible for turbidity in the developed color.

Magenta color image forming nuclei which can reduce the yellow component described above include pyrazolobenzimidazole nuclei as disclosed in British Patent 1,047,612, indazolone nuclei as disclosed in U.S. Pat. No. 3,770,447, pyrazolo(5,1-c)(1,2,4)triazole nuclei as disclosed in U.S. Pat. No. 3,725,067, pyrazolo(1,5-b)(1,2,4)triazole nuclei as disclosed in JP-A-59-171956 (the term "JP-A" as used herein means an "unexamined published Japanese patent application") and U.S. Pat. No. 4,540,654, and imidazo(1,2-b)pyrazole nuclei as disclosed in JP-A-59-162548 and U.S. Pat. No. 4,500,630.

Magenta couplers having in particular pyrazolo(1,5-b)(1,2,4)triazole nuclei are known to be superior with respect to light fastness of the color images produced therefrom, so they are favorable for use in color photographic paper, compared with magenta couplers having other nuclei. In order to bring couplers into practical use, however, the couplers must satisfy many other properties (e.g., hue inside of the film, color formability), in addition to the fastness of the color images produced. Therefore, various efforts for improvements have been made, and a large number of proposals on improvements thereto have been submitted. Examples of improvements to couplers include a method of adopting an aryloxy eliminating type (JP-A-61 53644), a method of introducing an alkoxy or an aryloxy group at the 6-position of a pyrazolotriazole nucleus (JP-A-62-209457), a method of introducing a phenylene group at the 2-position of said nucleus (JP-A-63-41851), and a method of designing a ballast group to be introduced (JP-A-61-065246, JP-A-61-147254, JP-A-62-89961, JP-A-62-125349). However, these methods are still insufficient to allow the general utilization of the above-described type magenta couplers in color photographic paper because the couplers proposed entail a high production cost, the couplers are not sufficiently stable, or the couplers have unsatisfactory hue.

SUMMARY OF THE INVENTION

Taking into account the high stability and the low production cost required couplers, the present inventors speculated that the most desirable substituent group to be located at the 6-position of a pyrazolotriazole nucleus must be an alkyl group and the most favorable coupling-eliminable group must be a halogen atom. Thus, the inventors have conducted an investigation in order to obtain couplers having properties suitable for practical use from members of the above-described series.

Accordingly, an object of the present invention is to develop a pyrazolo(1,5-b)(1,2,4)triazole type magenta coupler which can be widely applied to photosensitive materials and produced at a low cost, and which has excellent properties.

As a result of examining in detail the effects of substituent groups located at the 2- and 6-positions of a pyrazolotriazole nucleus in order to attain the above-described object, it has been found that proper selection of a combination of certain linkage and ballast groups as a substituent group at the 2-position, though the combination has a low molecular weight, allows the realization of desirable hue and excellent color formability.

Therefore, the present invention provides a silver halide color photographic material, which comprises a support having thereon at least one silver halide emulsion layer, at least one of said emulsion layers containing at least one nondiffusible pyrazolo(1,5-b)(1,2,4)triazole magenta coupler represented by the following general formula (I):

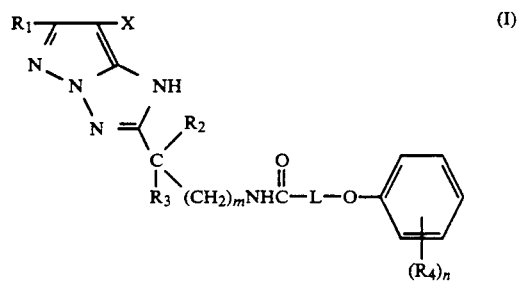

wherein $R_1$ represents an alkyl group; $R_2$ and $R_3$ each represent a hydrogen atom or an alkyl group, provided that both are not a hydrogen atom; $R_4$ represents an alkyl group, an alkoxy group or a halogen atom; L represents an alkylene group; m represents an integer of from 0 to 5; n represents an integer of from 0 to 5, and when n is 2 or more, the $R_4$'s may be different from one another; and X represents a halogen atom.

DETAILED DESCRIPTION OF THE INVENTION

General formula (I) is described below in detail.

$R_1$ represents a substituted or an unsubstituted alkyl group, preferably a straight or a branched-chain or a cyclic unsubstituted alkyl group containing 1 to 10 carbon atoms, more preferably an alkyl group such as methyl, ethyl, isopropyl, t-butyl, cyclohexyl or the like, and most preferably methyl groups.

$R_2$ and $R_3$ each represents a hydrogen atom, or a substituted or an unsubstituted alkyl group. As for the alkyl group, one which does not have a substituent group, contains 1 to 10 carbon atoms and assumes the form of a straight or a branched chain is preferred. Among the alkyl groups, methyl, ethyl, isopropyl, n-propyl, n-butyl and the like are favored over the others. In particular, the methyl group is desirable.

R4 represents a substituted or an unsubstituted alkyl group, a substituted or an unsubstituted alkoxy group, or a halogen atom. Preferably, R4 represents a straight or a branched-chain, or a cycloalkyl group containing 4 to 20 carbon atoms (in the alkyl moiety; the same hereinafter) (e.g., t-butyl, t-amyl, t-octyl, n-nonyl, n-pentadecyl, cyclohexyl, cyclopentyl), an alkoxy group containing 1 to 20 carbon atoms (e.g., methoxy, butoxy, ethoxyethoxy, hexylethoxy), a fluorine atom, a chlorine atom and a bromine atom. In further detail, these alkyl and alkoxy groups may be substituted by an aliphatic (including alycyclic) group (e.g., methyl, allyl, cyclopentyl), an aromatic group (e.g., phenyl, naphthyl), a heterocyclic group (preferably 5- or 6-membered heterocyclic group containing at least one of N, O and S atoms; the same hereinafter; e.g., 2-pyridyl, 2-imidazolyl, 2-furyl, 6-quinolyl), an aliphatic oxy group (e.g., methoxy, 2-methoxyethoxy, 2-propenyloxy), an aromatic oxy group (e.g., 2,4-di-tert-amylphenoxy, 4-cyanophenoxy, 2-colorphenoxy), an acyl group (e.g., acetyl, benzoyl), an ester group (e.g., butoxycarbonyl, phenoxycarbonyl, acetoxy, benzoyloxy, butoxysulfonyl, toluenesulfonyloxy), an amido group (e.g., acetylamino, methanesulfonamido), a carbamoyl group (e.g., ethylcarbamoyl, diethylcarbamoyl), a sulfamoyl group (e.g., butylsulfamoyl), an imido group (e.g., succinimido, hydantoinyl), a ureido group (e.g., phenylureido, dimethylureido), an aliphatic or aromatic sulfonyl group (e.g., methanesulfonyl, phenylsulfonyl), an aliphatic or an aromatic thio group (e.g., phenylthio, ethylethio), a hydroxyl group, a cyano group, a carboxyl group, a nitro group, a sulfo group, or a halogen atom (e.g., fluorine, chlorine, bromine). When an alkyl or an alkoxy group represented by R4 has two or more substituent groups, they may be the same or different. R4 may be substituted at any position, preferably R4 is substituted at o- and/or p-position.

In effect, it is desirable that R4 should be an alkyl group or a halogen atom. More preferably, R4 represents a branched-chain alkyl group, especially a t-amyl group.

L represents a substituted or an unsubstituted alkylene group preferably containing 1 to 20 carbon atoms in the alkylene moiety (e.g., methylene, ethylene, trimethylene, tetramethylene, dodecylmethylene). These alkylene groups may be substituted by any group so long as it is described above as a substituent group of R4. Alkylene groups preferred as L are represented by the formula,

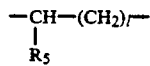

wherein R5 represents a hydrogen atom, or a straight or a branched-chain alkyl group containing 1 to 30 carbon atoms; and l is an integer of from 0 to 10. More preferably L contains R5 as a straight or a branched-chain alkyl group containing 2 to 20 carbon atoms and l as an integer of 0 to 5, and in particular, R5 should be a straight-chain alkyl group containing 4 to 10 carbon atoms and l should be 0.

m represents an integer of 0 to 5, preferably 0 or 1, and more preferably 1.

n represents an integer of 1 to 5, preferably 1 or 2, and more preferably 2.

X represents a halogen atom, preferably a fluorine atom or a chlorine atom, and more preferably a chlorine atom.

Furthermore, it is necessary that this coupler is not moved from the coated layer during the coating of the emulsified dispersion containing the coupler or during the photographic processing of the exposed photosensitive material. In order to impart sufficient diffusion resistance to the coupler, it is desirable that the total number of carbon atoms contained in L and (R4)n should be 10 or above, especially 17 or above.

Specific examples of typical magenta couplers represented by general formula (I) are illustrated below. However, the invention should not be construed as being limited to these representative examples. (In the present invention, when an alkyl group in a chemical formula is not shown with (n), (t) or (iso), the alkyl group should be considered as n-alkyl group.)

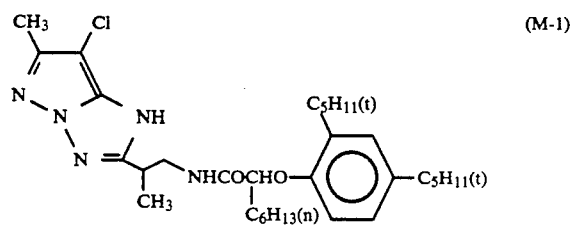
(M-1)

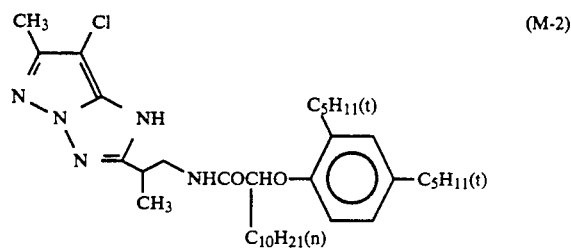
(M-2)

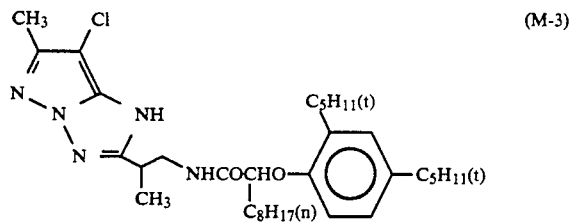
(M-3)

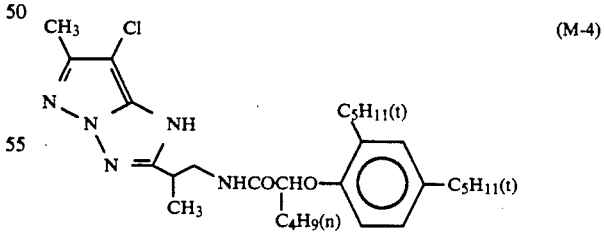
(M-4)

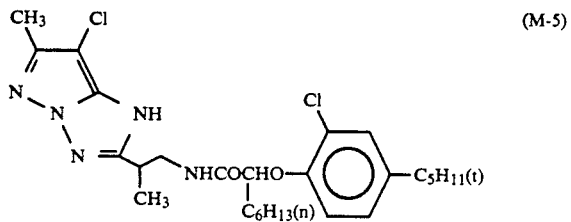
(M-5)

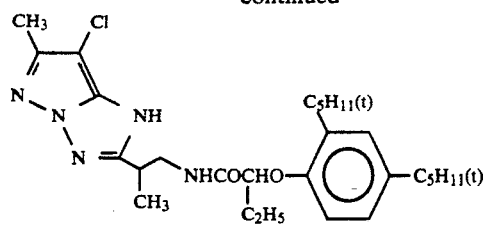 (M-6)
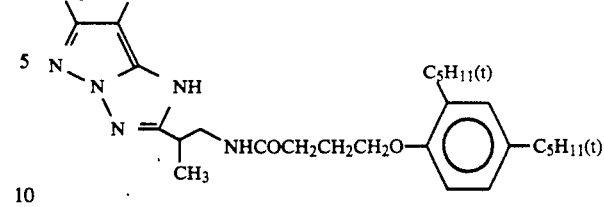 (M-13)
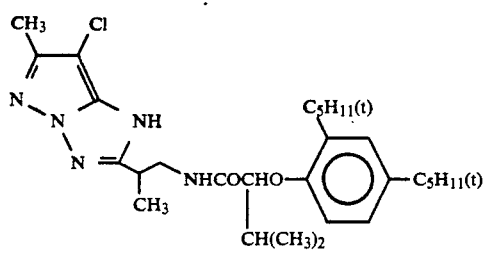 (M-7)
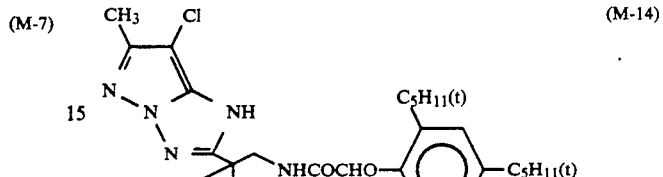 (M-14)
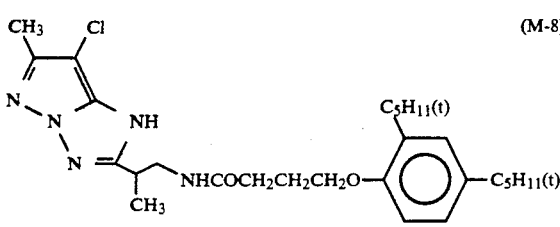 (M-8)
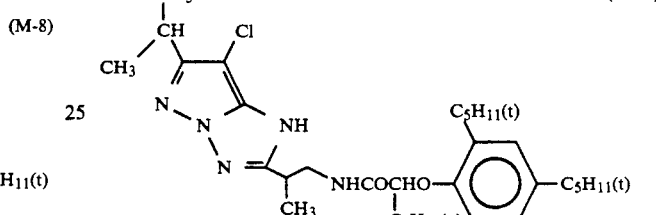 (M-15)
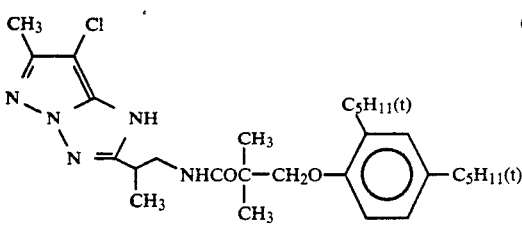 (M-9)
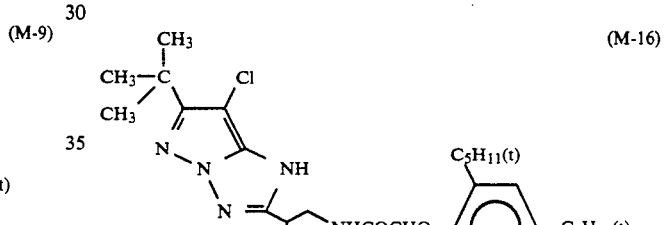 (M-16)
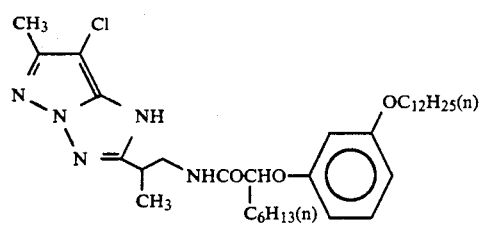 (M-10)
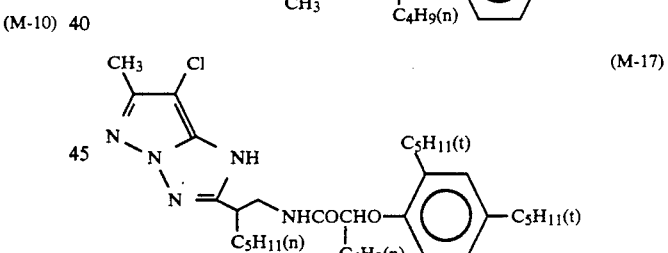 (M-17)
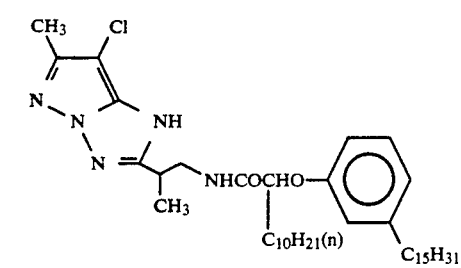 (M-11)
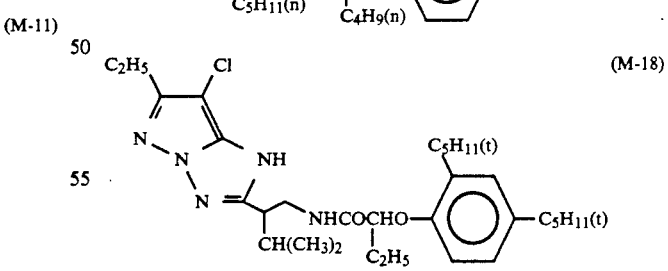 (M-18)
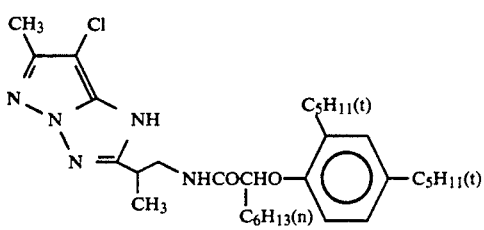 (M-12)
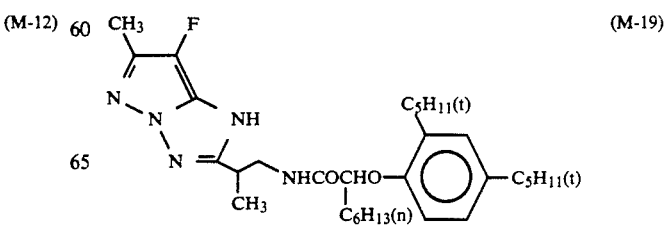 (M-19)

(M-20) 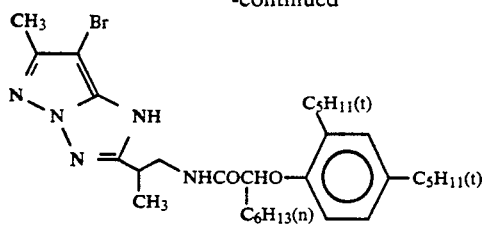
(M-21) 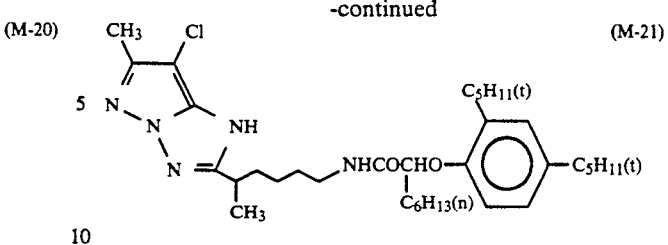
The general synthesis methods of the coupler of the present invention are described hereinbelow.
The coupler of the present invention can be synthesized using methods as described in JP-A-60-197688, JP-A-61-145163, JP-A-63-218664, JP-A-63-239272, and so on. A general synthesis route is illustrated by the following scheme (1):
Scheme 1
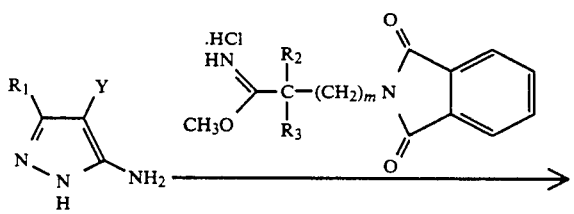
(Y = hydrogen or halogen atom)
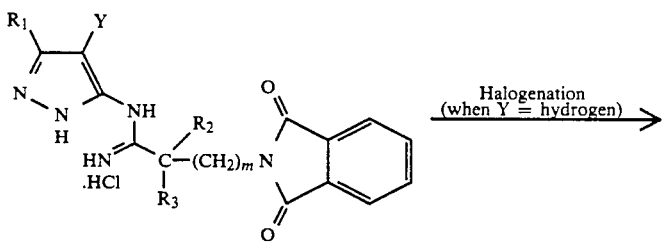
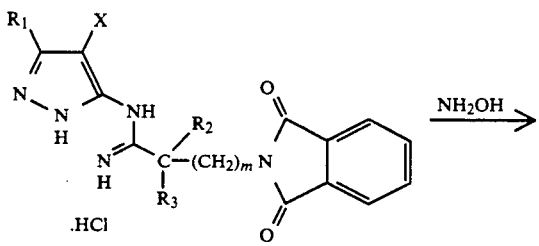
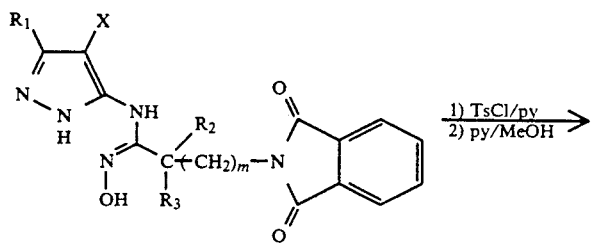

Scheme 1

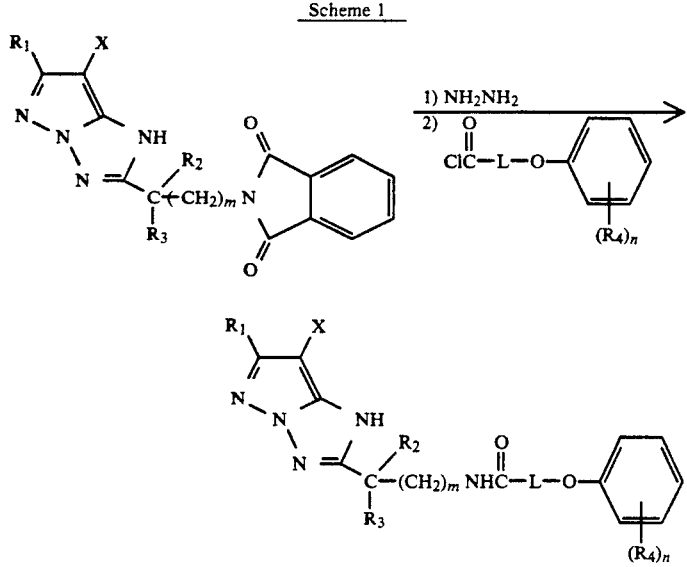

General formula (I)

Each process step in the foregoing synthesis route proceeds with a very high yield, so the couplers represented by general formula (I) are excellent from the view point of production and they can be produced at low cost.

A specific example of the synthesis of a coupler of the invention is shown below, wherein the above-described point is illustrated in further detail.

SYNTHESIS EXAMPLE

Synthesis of Coupler (M-1)

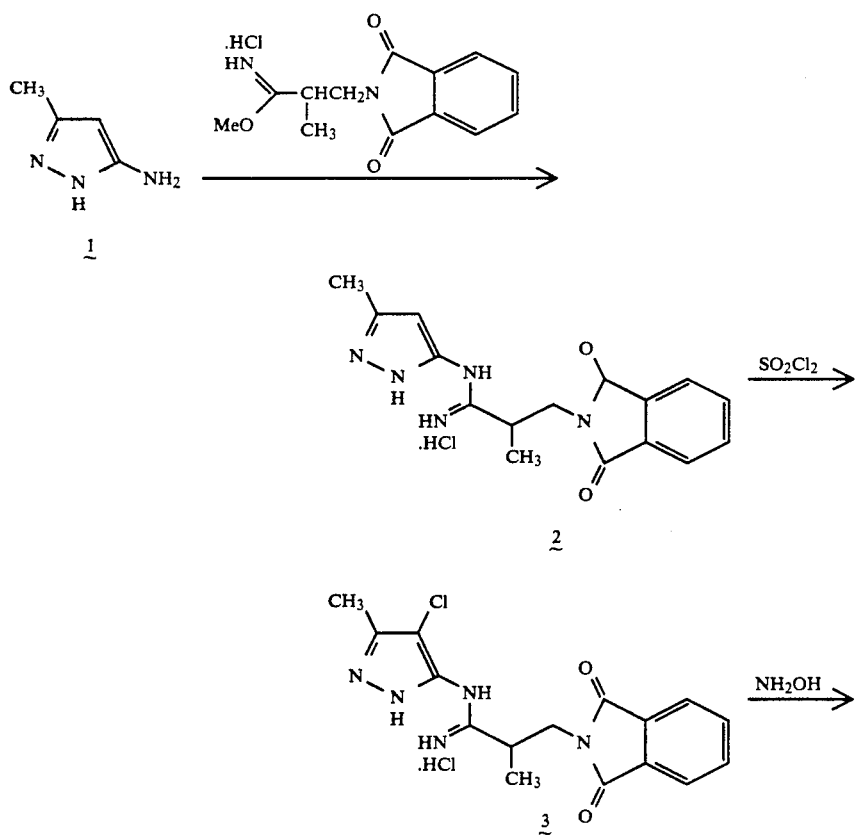

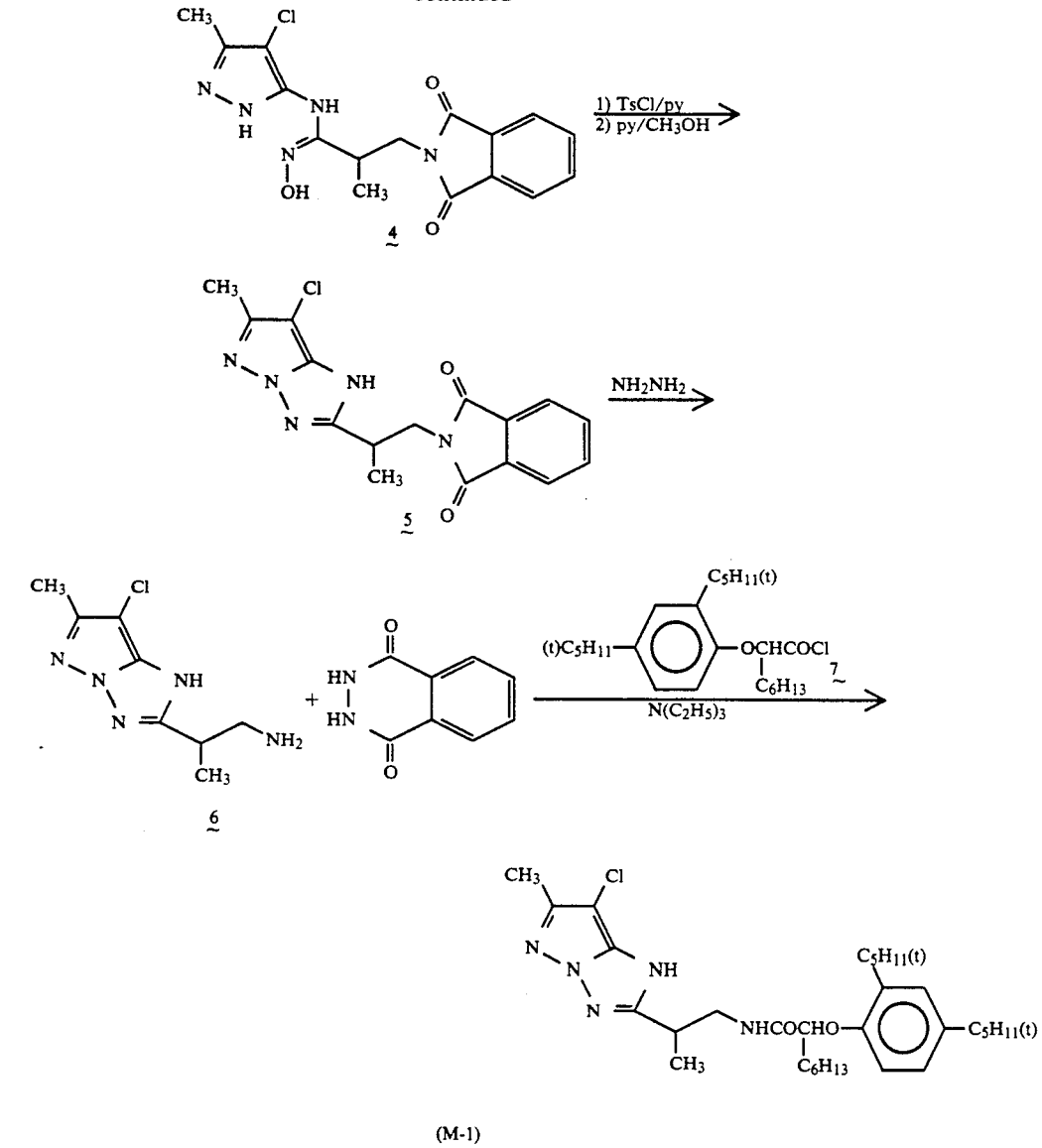

(M-1)

In acetonitrile, 50 g (0.51 mol) of 5-amino-3-methylpyrazole (1) was made to react with 173 g (0.61 mol) of 2-methyl-3-phthalimidopropionimino acid methyl ester hydrochloride (prepared from 2-methyl-3-phthalimidopropionitrile obtained by reacting methacrylonitrile with phthalimide in the presence of a base according to Pinner's method) to yield crystals of amidine hydrochloride (2). These crystals are filtered off and dried to give 141 g (a 81% yield) of the intended amidine hydrochloride, mp. ~225° C. (decomposed).

A 139 g (0.40 mol) portion of this amidine hydrochloride was dissolved in 240 ml of N,N-dimethylformamide and cooled in an ice bath. 35.4 ml (0.44 mol) of sulfuryl chloride was added dropwise thereto while stirring. Then, the reaction system was taken out of the ice bath and the stirring was further continued for one hour. A solution containing 83.4 g (1.2 mol) of hydroxylamine hydrochloride and 131.2 g (1.6 mol) of sodium acetate in 1.8 liters of water was added thereto at room temperature, and heated for 2 hours while stirring over a steam bath. After cooling in a water bath, the crystalline precipitate was filtered off, washed with water, and air-dried to obtain 118.6 g (82%) of amidoxime (4) mp. 211° C. (decomposed).

A 101 g (0.28 mol) portion of this amidoxime (4) was dissolved in 90 ml of N,N-dimethylacetamido, admixed with 90 ml of acetnnitrile, and stirred. 53 g (0.28 mol) of p-toluenesulfonyl chloride and 23 ml (0.28 mol) of pyridine were further added thereto, and stirred under water-cooling to synthesize the tosylate. After about one hour, 700 ml of methanol and 23 ml (0.28 mol) of pyridine were added directly to the reactant solution and heated under reflux for about 2 hours. The resulting solution was concentrated to about 100 ml and poured into 700 ml of water to precipitate the crystals. These crystals were filtered off, heated in 140 ml of methanol, cooled to room temperature, and filtered off again. Thus, 82 g (a 85% yield) of the compound (5), mp 123 to 126° C., was obtained.

Further, 17 ml (0.28 ml) of a 80% hydrazine hydrate was poured into a solution containing 80 g (0.23 mol) of compound (5) in 200 ml of isopropanol and heated under reflux for about 4 hours. After cooling to room temperature, the deposited crystals were filtered off, washed with acetonitrile, and air-dried to obtain compound (6) in an amount of 80 g (a 92% yield).

100 ml of N,N-di-dimethylacetamide and 100 ml of ethyl acetate were added to a 60 g (0.16 mol) portion of the thus obtained compound (6), and the resulting mixture was cooled in an ice bath while stirring. 60 g (0.15 mol) of the acid chloride (7) was added dropwise thereto. After the conclusion of the addition step, 21.2 ml (0.15 mol) of triethylamine was further added dropwise thereto. Thereafter, the reaction mixture was cooled to room temperature, further stirred for 2.5 hours, admixed with water, and then extracted with ethyl acetate. The extract was washed successively twice with an aqueous solution of sodium bicarbonate, once with a dilute aqueous solution of hydrochloride, and twice with a saturated solution of sodium chloride, dried over anhydrous sodium sulfate, and concentrated. The thus obtained oily matter was crystallized from solution in a mixture of acetonitrile and ethyl acetate to obtain 86 g (a 94% yield) of the desired compound (M-1), mp 118 to 120° C.

The foregoing Pinner's method is described in detail in the following representative literature references:

S.R. Sandler & W. Karo, *Organic Functional Group Preparations*, vol. 3, Chapt. 8, Academic Press (1972); and H. Henecka & P. Kurts, *Methoden der Organischen Chemie* (*Houben-Weyl*), Band VIII, p. 697 to 701, Georg Thieme (1952).

The color photographic light-sensitive material of the present invention can be made by coating over a support at least one blue-sensitive silver halide emulsion layer, at least one green-sensitive silver halide emulsion layer and at least one red sensitive silver halide emulsion layer. In a typical color photographic paper, such emulsion layers are usually coated over a support in the above-described order, but these layers may be coated in any order other than the above-described order. In these light-sensitive emulsion layers, the reproduction of colors by a subtractive color process can be effected by combining silver halide emulsions having sensitivity in their individual wavelength regions and so-called color couplers in the emulsion layers. Each of these color couplers in the emulsion layers forms a dye bearing a complementary color relationship to the light of specific wavelengths to which any one of the emulsions has color sensitivity, i.e., a yellow color-forming coupler to blue light, a magenta color-forming coupler to green light and a cyan color-forming coupler to red light. However, the color sensitivity of each light-sensitive layer and the hue of the dye formed by a coupler used in combination may bear relationships other than described above. For instance, a combination of an infrared-sensitive layer and, for example, a cyan coupler, a combination of a red-sensitive layer and a magenta coupler, and other various combinations can be employed.

When the sensitive material of the present invention is used as a color photographic paper, the silver halide emulsions to be used preferably comprise silver chlorobromide or silver chloride having no iodide content in a substantial sense. The expression "having no iodide content in a substantial sense" signifies an iodide content of 1.0 mol% or less, preferably 0.2 mol% or less.

On the other hand, when the sensitive material of the present invention is used as a negative film for taking photographs, as a color reversal film, or as a sensitive material using direct positive emulsions, the silver halides which can preferably be used include silver bromide and silver iodobromide in addition to the above-described ones. The emulsion which is used may have some differences in the halogen composition among the emulsion grains, or each individual grain in the emulsion which is used may have the same halogen composition as every other individual grain. However, when all the grains in the emulsion which is used have the same halogen composition, it is easy to render uniform properties to the grains. As for the distribution of the halogen compositions inside the individual silver halide emulsion grains, each grain may take any structure, if desired. For instance, the grains may have a so-called uniform structure so that the halogen composition is the same in every part of the grain, a so-called laminate structure so that there is a difference in the halogen composition between the inner part of the silver halide grain (core) and the core-encircling part (shell) which may have one or more constituent layers, or the grains may have such a structure that parts differing in the halogen composition from the surroundings are present in a nonstratified condition at the interior or at the surface of the grain (in the case that such parts are present at the grain surface, a junction of the parts different in halogen composition from each other is present on an edge, a corner or a face of the grain). In order to achieve a high sensitivity, both the latter two structures are advantageously employed, compared with the former uniform structure. The latter two non-uniform structures are preferred with respect to pressure resistance, too. When each silver halide grain has a non-uniform structure as described above, the interface between the parts different in halogen composition may have a definite boundary, a boundary rendered vague by the formation of mixed silver halides whose halogen compositions vary with locality by small degrees, or a positively introduced continuous structural change.

As for the halogen composition of the silver chlorobromide emulsions, the content of the silver bromide may bear any ratio to that of the silver chloride. Although the silver bromide/silver chloride ratio can vary widely according to the intended purpose, silver chlorobromides having a silver chloride content of 2% or more are advantageously used.

Also, silver halide emulsions having a high silver chloride content (called high silver chloride content emulsions for short) are preferably used in preparing photosensitive materials suitable for rapid processing. A preferred silver chloride content in the high silver chloride content emulsions is 90 mol% or more, particularly 95 mol% or more. In order to obtain high sensitivity and reduced fog, silver chlorobromide emulsions having a silver chloride content of 98 to 99.9 mol% are preferred.

In these high silver chloride content emulsions, it is desirable that individual emulsion grains should take such a structure as to have a silver bromide-localized phase in a stratified or non-stratified form at the interior or surface of the grains. As for the halogen composition in the above-described localized phase, the fraction of silver bromide is preferably at least 10 mol%, and more preferably above 20 mol%. Such a localized phase as described above can be present inside the grain, or on an edge, a corner or a face of the grain surface. For instance, a preferable example is where the silver bromide-localized phase is formed by epitaxial growth on the corners of the grain surface.

On the other hand, in order to minimize the drop in sensitivity caused in photosensitive materials when pressure is applied thereto, it is preferable even in high silver chloride content emulsions having a silver chloride content of 90 mol% or above that a distribution of halogen compositions inside the individual grains should be narrow, that is to say, each grain should have a uniform structure.

Also, for the purpose of reducing the amount of replenisher in development processing, it is effective to further increase the silver chloride content in the silver halide emulsions. In such a case, emulsions comprising almost pure silver chloride, or having a silver chloride content of 98 to 100 mol% are preferably employed.

An average grain size of the silver halide grains contained in the silver halide emulsions to be used in the present invention preferably ranges from 0.1 to 2 μm. The average grain size is expressed in terms of the number average of diameters of the circles having the same areas as the projected areas of the individual grains.

In addition, so-called monodisperse emulsions having a variation coefficient of 20% or less, especially 15% or less, in grain size distribution (which is defined as a value obtained by dividing the standard deviation of the grain sizes by the average grain size) are preferred. In order to attain wide latitude, it is advantageous to use two or more kinds of monodisperse emulsions in a single layer in a blended form, or to coat such emulsions in the form of a multilayer coating.

Silver halide grains contained in the photographic emulsions may have a regular crystal form, such as that of a cube, tetradecahedron, octahedron, etc., an irregular crystal form, such as that of a sphere, a plate, etc., or a composite form of these crystal forms. Also, a mixture of grains having different crystal forms can be used. In such a mixture, it is desirable that grains having a regular crystal form should be contained in a fraction of 50% or more, preferably 70% or more, and more preferably 90% or more.

In addition, silver halide emulsions which can preferably be used in the present invention include such emulsions which contain tabular grains having an average aspect ratio (diameter of circle obtained by conversion/thickness ratio) of 5 or more, particularly 8 or more, in a fraction of 50% or more, based on the projected area of the whole grains.

The chlorobromide emulsions to be used in the present invention can be prepared using methods as described in P. Glafkides, *Chemie et Phisique Photographique*, Paul Montel, (1967), G.F. Duffin, *Photographic Emulsion Chemistry*, The Focal Press, (1966), V.L. Zelikman et al, *Making and Coating Photographic Emulsion*, The Focal Press, (1964), and so on. For example, an acid process, a neutral process, an ammonia process and other conventional processes may be employed, and suitable methods for reacting a water-soluble silver salt with a water-soluble halide include a single jet method, a double jet method and a combination thereof. Also, a method in which silver halide grains are produced in the presence of excess silver ion (the so-called reversal mixing method) can be employed. On the other hand, the so-called controlled double jet method, wherein the pAg of the liquid phase in which the silver halide grains are to be formed is maintained constant, can also be employed. According to this method, a silver halide emulsion which contains grains having a regular crystal form and which is nearly uniform in grain size can be obtained.

In a process for producing the emulsion grains of the silver halide emulsions of the present invention, or during the process of allowing the produced grains to ripen physically, various kinds of polyvalent metal ions can be introduced as impurities. Examples of compounds usable for the above-described purpose include cadmium salts, zinc salts, lead salts, copper salts, thallium salts, and salts or complexes of Group VIII elements in the Periodic Table, such as iron, ruthenium, rhodium, palladium, osmium, iridium, platinum and the like. In particular, the above-cited Group VIII elements are favored over the others. These compounds can be added in amounts varying over a wide range depending on the intended purpose, but desirable amounts range from $10^{-9}$ to $10^{-2}$ mole per mole of silver halide.

Silver halide emulsions to be used in the present invention are, in general, subjected to chemical sensitization and spectral sensitization.

As for the chemical sensitization, sulfur sensitization represented by the addition of an unstable sulfur compound, noble metal sensitization represented by gold sensitization, reduction sensitization and so on can be used individually or in combination of two or more thereof. Compounds which can preferably be used for chemical sensitization include those described in JP-A-62-215272, from the lower right column on page 18 to the upper right column on page 22.

Spectral sensitization is carried out for the purpose of imparting spectral sensitivities in a desired wavelength region to an emulsion of each layer in the photosensitive material of the present invention. In the present invention, it is desirable that spectral sensitization should be effected by the addition of dyes or spectral sensitizing dyes capable of absorbing light of wavelengths which correspond to the desired spectral sensitivities. Examples of spectral sensitizing dyes which can be used therein include those described, for example, in F.H. Harmer, *Heterocyclic Compounds-Cyanine Dyes and Related Compound*, John Wiley & sons, New York, London (1964). Specific examples of compounds which can be preferably used for spectral sensitization include those described in the above-cited patent JP-A-62-215272, from the upper right column on page 22 to page 38.

The silver halide emulsions to be used in the present invention can contain a wide variety of compounds or precursors thereof for the purpose of preventing fogging or for stabilizing photographic functions during production, storage or photographic processing of the photosensitive material. Such compounds are generally called photographic stabilizers. Specific examples of photographic stabilizers which can advantageously be used include compounds described in the above-cited patent JP-A-62-215272, from page 39 to page 72.

Emulsions to be used in the present invention may be either the so-called surface latent-image type emulsions which form a latent image predominantly at the surface of the grains, or the so-called internal latent image type emulsions which form a latent image predominantly inside the grains.

In color photographic materials, yellow couplers, magenta couplers and cyan couplers, which produce yellow, magenta and cyan colors, respectively, by coupling with the oxidation product of an aromatic amine color developer, are generally used.

Among the yellow couplers which can be used in the present invention, acylacetamide derivatives such as benzoylacetanilides and pivaloylacetanilides are preferred over the others.

In particular, yellow coupler represented by the following general formulae (Y-1) and (Y-2) are used to great advantage:

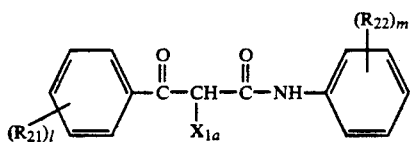

wherein $X_{1a}$ represents a hydrogen atom, or a coupling eliminable group; l and m each represents an integer of 1 to 5; $R_{21}$ and $R_{22}$ each represents a hydrogen atom or a substituent such as a halogen atom, a lower alkyl group, a lower alkoxy group or a nondiffusible group having a total of 8 to 32 carbon atoms; at least one of $R_{21}$ and $R_{22}$ represents a nondiffusible group having a total of 8 to 32 carbon atoms; when l and m is 2 or more and $R_{21}$ or $R_{22}$ is a substituent, the total of these substituents may form a nondiffusible group having a total of 8 to 32 carbon atoms.

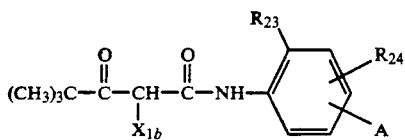

wherein $R_{23}$ represents a halogen atom, an alkyl group, an alkoxy group, a trifluoromethyl group, an aryl group, an aryloxy group, a dialkylamino group, an alkylthio group or an arylthio group; $R_{24}$ represents a hydrogen atom, a halogen atom, or an alkoxy group; A represents -NHCOR$_{25}$, -NHSO$_2$R$_{25}$, -SO$_2$NHR$_{25}$, -COOR$_{25}$, or

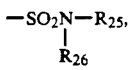

wherein $R_{25}$ and $R_{26}$ each represents an alkyl group, an aryl group or an acyl group; $X_{1b}$ represents an eliminable group; at least one of $R_{23}$, $R_{24}$ and A or total thereof is a nondiffusible group having a total of 8 to 32 carbon atoms. Preferably, $X_{1b}$ is an oxygen atom-eliminating or a nitrogen atom-eliminating type group, and a nitrogen atom-eliminating type group is especially preferred.

Details of pivaloylacetanilide type yellow couplers are described in U.S. Pat. No. 4,622,287, from line 15 in column 3 to line 39 in column 8, and U.S. Pat. No. 4,623,616, from line 50 in column 14 to line 41 in column 19.

Details of benzoylacetanilide yellow couplers are described, for example, in U.S. Pat. Nos. 3,408,194, 3,933,501, 4,046,575, 4,133,958, and 4,401,752.

Specific examples of pivaloylacetanilide yellow couplers include Compounds (Y-1) to (Y-39) disclosed in the above-cited U.S. Pat. No. 4,622,287, from column 37 to column 54. In particular, (Y-1), (Y-4), (Y-6), (Y-7), (Y-15), (Y-21), (Y-22), (Y-23), (Y-26), (Y-35), (Y-36), (Y-37), (Y-38) and (Y-39) are preferably employed in the present invention.

In addition, Compounds (Y-1) to (Y-33) disclosed in the above-cited U.S. Patent 4,623,616 can be used in the present invention. In particular, (Y-2), (Y 7), (Y-8), (Y-12), (Y 20), (Y-21), (Y 23) and (Y-29) are preferred in the present invention.

Other specific examples of yellow couplers which can preferably be used in the present invention include Compound Example (34) disclosed in U.S. Pat. No. 3,408,194, column 6; Compound Examples (16) and (19) disclosed in U.S. Pat. No. 3,933,501, column 8; Compound Example (9) disclosed in U.S. Pat. No. 4,046,575, columns 7 to 8; Compound Example (1) disclosed in U.S. Pat. No. 4,133,958, columns 5 to 6; Compound Example 1 disclosed in U.S. Pat. No. 4,401,752, column 5; and the compounds a) to k) illustrated below:

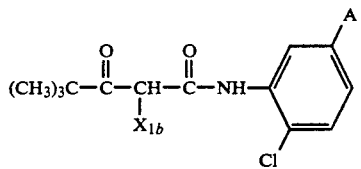

| Compound Example | A | $X_{1b}$ |
|---|---|---|
| a | $\begin{array}{c} CH_3 \\ | \\ -COOCHCOOC_{12}H_{25} \end{array}$ | O=⟨N⟩=O, N—N—CH$_2$—Ph (phenyl groups) |
| b | $\begin{array}{c} C_4H_9 \\ | \\ -COOCHCOOC_{12}H_{25} \end{array}$ | " |

-continued

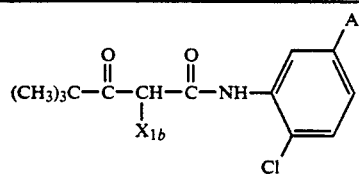

| Compound Example | A | $X_{1b}$ |
|---|---|---|
| c | —NHCO(CH$_2$)$_3$O—(2,4-di-t-C$_5$H$_{11}$-phenyl) | —O—C$_6$H$_4$—SO$_2$—C$_6$H$_4$—OCH$_2$—C$_6$H$_5$ |
| d | " | 2-(p-tolylsulfonamido)-5-isopropyl-1,3,4-thiadiazol-2-yl (N-methyl) |
| e | —NHCO(CH$_2$)$_3$O—(2,4-di-t-C$_5$H$_{11}$-phenyl) | 1-methyl-5-(hexyloxycarbonyl)imidazol-4-yl |
| f | —NHSO$_2$C$_{12}$H$_{25}$ | —O—C$_6$H$_4$—COOCH(CH$_3$)$_2$ |
| g | —NHSO$_2$C$_{16}$H$_{33}$ | 1-methyl-3-morpholino-1,2,4-triazol-5-yl |
| h | —NHCOCH(CH$_3$)CH$_2$SO$_2$C$_{12}$H$_{25}$ | 1-methyl-3-(N-benzyl)-hydantoin-5-yl |
| i | —NHCOCH[CH(CH$_3$)CH$_2$C(CH$_3$)$_3$][CH$_2$CH(CH$_3$)CH$_2$C(CH$_3$)$_3$] | 1-methyl-3-benzyl-5-ethoxy-hydantoin-5-yl |
| j | " | 1,5,5-trimethylhydantoin-3-yl |

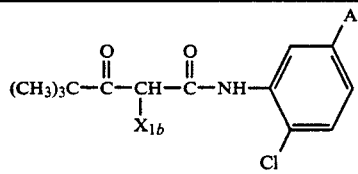

| Compound Example | A | $X_{1b}$ |
|---|---|---|
| k | | 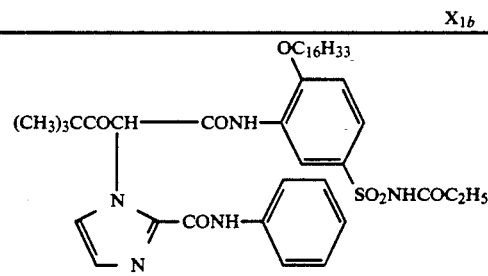 |

Of the above-cited couplers, those containing a nitrogen atom as the eliminating atom are particularly preferred.

The magenta coupler of the present invention can be used together with other magenta couplers, preferably in an amount of up to 50 mol% based on the total amount of the magenta couplers in an emulsion layer. Suitable examples of magenta couplers which can be used in combination include those of the oil-protected indazolones or cyanoacetyl compounds, more preferably those of the 5-pyrazolones and those of the pyrazoloazoles, such as pyrazolotriazoles. As for the 5-pyrazolone type couplers, those having an arylamino group or an acylamino group at the 3-position are advantageous with respect to the hue and density of the developed colors, and representative examples thereof are described in U.S. Pat. Nos. 2,311,082, 2,343,703, 2,600,788, 2,908,573, 3,062,653, 3,152,896, 3,936,015, and so on. Suitable examples of coupling eliminable groups of two-equivalent 5-pyrazolone couplers include those having a nitrogen atom-eliminating group, as disclosed in U.S. Pat. No. 4,310,619; and the arylthio groups disclosed in U.S. Pat. No. 4,351,897 and WO 88/04795. Also, a high density of the developed color is obtained by the ballast group-containing 5-pyrazolone couplers disclosed in European Patent 73,636.

Suitable examples of pyrazoloazole couplers include the pyrazolobenzimidazoles disclosed in U.S. Pat. No. 2,369,879, and preferably the pyrazolo(5,1-c)(1,2,4)triazoles disclosed in U.S. Pat. No. 3,725,067, the imidazo(1,2-b)pyrazoles disclosed in U.S. Pat. No. 4,500,630, the pyrazolotetrazoles described in Research Disclosure, 24220 (Jun. 1984) and the pyrazolopyrazoles described in Research Disclosure, 24230 (Jun. 1984). All of the above-described couplers may assume a polymerized form.

More specifically, the compounds described above are represented by the following general formulae (M'-1), (M'-2) and (M'-3), respectively:

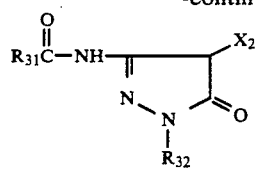 (M'-1)

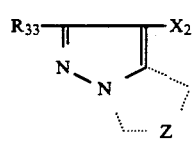 (M'-2)

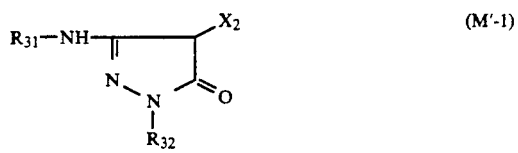 (M'-3)

wherein $R_{31}$ represents a nondiffusible group containing a total of 8 to 32 carbon atoms; $R_{32}$ represents a phenyl group or a substituted phenyl group; $R_{33}$ represents a hydrogen atom or a substituent group; Z represents nonmetal atoms necessary to complete a 5-membered azole ring containing 2 to 4 nitrogen atoms, which may have a substituent group (including a condensed ring); $X_2$ represents a hydrogen atom or a group capable of eliminating. The couplers represented by formula (I) are not included in formula (M'-3).

Details of the substituent groups represented by $R_{33}$ and details of the substituent groups of the azole ring are described, for instance, in U.S. Pat. No. 4,540,654, from line 41 in column 2 to line 27 in column 8.

Of the pyrazoloazole couplers, those which are favorable because the side absorption in the yellow region is small and the fastness to light is high include the imidazo(1,2-b)pyrazoles disclosed in U.S. Pat. No. 4,500,630, and those which are particularly preferred over the others with respect to these properties are the pyrazolo(1,5-b)(1,2,4)triazoles disclosed in U.S. Pat. No. 4,540,654.

Examples of other favorable pyrazoloazole couplers include pyrazolotriazole couplers having a branched alkyl group attached directly to the 2-, 3- or 6- position of the pyrazolotriazole ring, as disclosed in JP-A-61-65245; pyrazoloazole couplers containing a sulfonamido group in a molecule, as disclosed in JP-A-61-65245; pyrazoloazole couplers containing an alkoxyphenylsulfonamido group as a ballast group, as disclosed in JP-A-61-147254; and pyrazolotriazole couplers having an alkoxy group or an aryloxy group at the 6-position, as disclosed in European Patents (unexamined published) 226,849 and 294,785.

Specific examples of the above-described couplers are illustrated below:

| Compound | R₃₃ | R₃₄ | X₂ |
|---|---|---|---|
| m-1 | CH₃— | 4-OC₈H₁₇, 3-(CHCH₂NHSO₂—)(CH₃)-phenyl-NHSO₂-[2-OC₈H₁₇-5-C₈H₁₇(t)-phenyl] | Cl |
| m-2 | " | -CH(CH₃)CH₂NHSO₂-[2-OCH₂CH₂OC₆H₁₃(n)-5-C₈H₁₇(t)-phenyl] | " |
| m-3 | (CH₃)₃C— | -CH₂CH₂NHCOCH(C₂H₅)-[2-C₅H₁₁(t)-4-C₅H₁₁(t)-phenyl] | 4-methoxyphenyl |
| m-4 | 2-OCH₃-phenyl | 3-(NHSO₂-p-tolyl)-[2-OC₈H₁₇-5-C₈H₁₇(t)-phenyl] | 2-OC₄H₉-5-C₈H₁₇(t)-phenylthio |

-continued
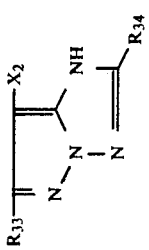
| Compound | $R_{33}$ | $R_{34}$ | $X_2$ |
|---|---|---|---|
| m-5 | $CH_3-$ | (structure) | Cl |
| m-6 | (structure) | (structure) | |

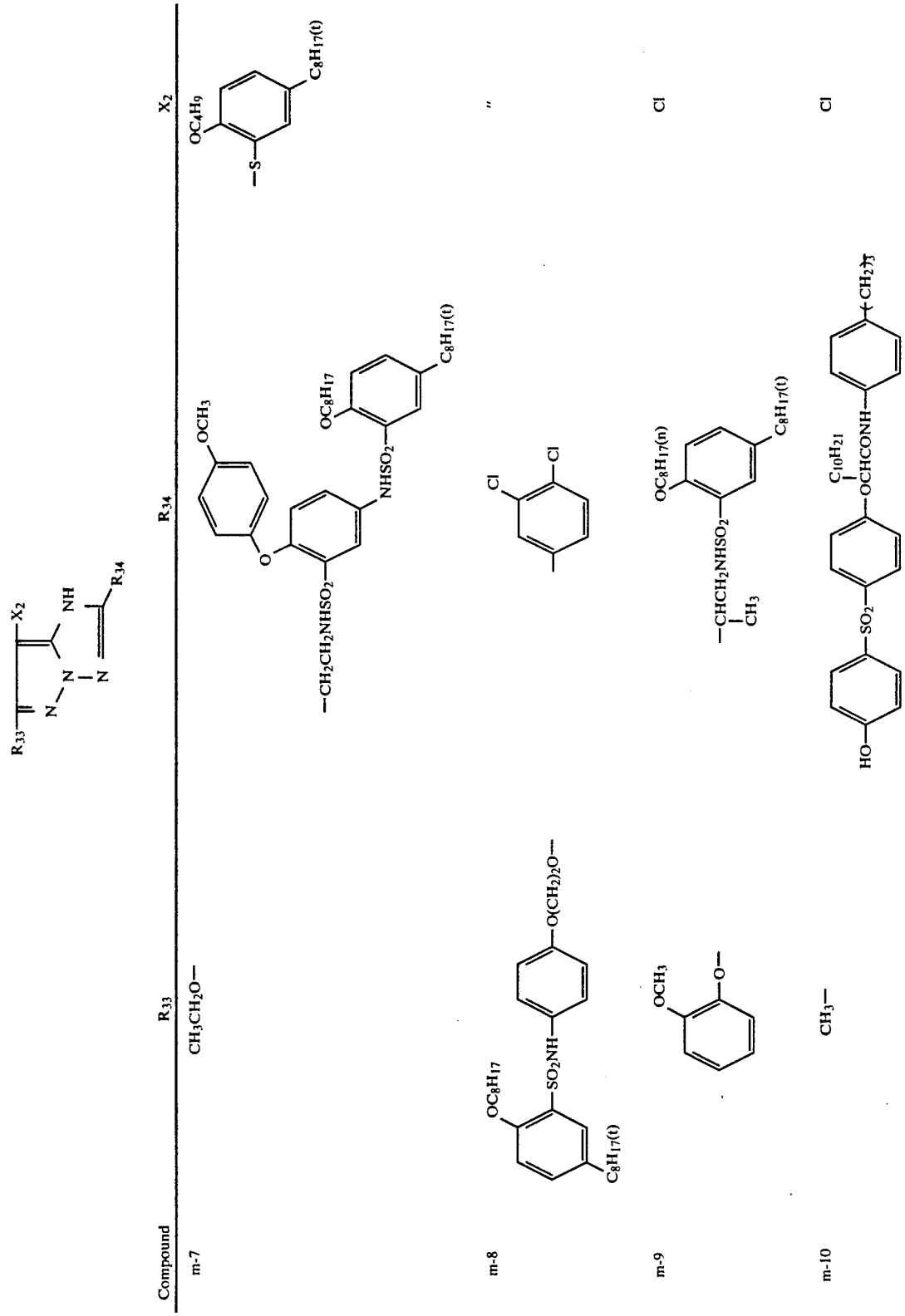

-continued $$\begin{array}{c} X_2 \\ R_{33} \overset{|}{\underset{N}{\diagdown}} \overset{NH}{\underset{N}{\diagdown}} R_{34} \end{array}$$

| Compound | $R_{33}$ | $R_{34}$ | $X_2$ |
|---|---|---|---|
| n-11 | " | $\underset{(n)C_8H_{17}}{\overset{(n)C_6H_{13}}{\text{CHCH}_2\text{SO}_2\text{+CH}_2\text{+}_7}}$ | " |
| m-12 | $\underset{CH_3}{\overset{CH_3}{\diagdown}}\!\!CH-$ | 4-OC$_4$H$_9$, 3-SO$_2$+CH$_2$+$_3$, C$_8$H$_{17}$(t)-phenyl | " |
| m-13 | +CH—CH$_2$+$_{50}$+CH$_2$—C(CH$_3$)+$_{50}$CONH—<br>COOCH$_2$OCH$_3$<br>(Suffixes of parentheses show a weight ratio.) | CH$_3$—CH—CH$_2$NHSO$_2$CH$_3$ | " |
| m-14 | phenoxy | 2-OC$_8$H$_{17}$, 5-C$_8$H$_{17}$(t), 1-(CH$_2$)$_2$NHSO$_2$— | Cl |
| m-15 | CH$_3$— | 2,4,6-trimethyl-3-NHCOCH(nC$_{10}$H$_{21}$)O-C$_6$H$_4$-SO$_2$-C$_6$H$_4$-OCH$_2$-C$_6$H$_5$ | " |

-continued $$R_{33}\underset{N-N}{\overset{X_2}{\underset{|}{C}}}\underset{}{\overset{NH}{\underset{|}{C}}}R_{34}$$

| Compound | R₃₃ | R₃₄ | X₂ |
|---|---|---|---|
| m-16 | (CH₃)₃C— | ![structure: 2,4,6-trimethylphenyl with NHCOCH(C₂H₅)-O-2-(t)C₅H₁₁-4-C₅H₁₁ phenyl] | " |
| m-17 | 2,5-dimethoxy-3-methylphenyl | —(CH₂)₂O— phenyl with 2-C₅H₁₁(t), 4-C₅H₁₁(t) | " |
| m-20 | CH₃— | (n)C₁₈H₃₇—CH(C₂H₅)—NCOCH₂CH₂COOH | " |
| m-21 | CH₃— | —CH(C₁₂H₂₅)O-phenyl-NHSO₂-phenyl-3-COOH | " |

Representative cyan couplers are phenol cyan couplers and naphthol cyan couplers.

Examples of phenol cyan couplers include those having an acylamino group and an alkyl group at the 2- and the 5-positions of a phenol nucleus, respectively (in which polymeric couplers are included), as disclosed in U.S. Pat. Nos. 2,369,929, 4,518,687, 4,511,647, 3,772,002, and so on. Typical examples of such couplers include the coupler used in Example 2 of Canadian Patent 625,822, Compound (1) disclosed in U.S. Pat. No. 3,772,002, Compounds (I-4) and (I-5) disclosed in U.S. Pat. No. 4,564,590, Compounds (1), (2), (3) and (24) disclosed in JP-A-61-39045, and Compound (C-2) disclosed in JP-A-62-70846.

Other examples of phenol cyan couplers include 2,5-diacylaminophenol couplers disclosed in U.S. Pat. Nos. 2,772,162, 2,895,826, 4,334,011 and 4,500,653, and JP-A-59-164555. 59-164555. Typical examples of such couplers are Compound (V) disclosed in U.S. Pat. No. 2,895,826, Compound (17) disclosed in U.S. Pat. No. 4,557,999, Compound (2) and (12) disclosed in U.S. Pat. No. 4,565,777, Compound (4) disclosed in U.S. Pat. No. 4,124,396, and Compound (I-19) disclosed in U.S. Pat. No. 4,613,564.

Additional examples of phenol cyan couplers include condensed-ring compounds formed by condensing a phenol nuclei and nitrogen-containing hetero rings, as disclosed in U.S. Pat. Nos. 4,372,173, 4,564,586 and 4,430,423, JP-A-62-390441, and JP-A-62-257158. Typical examples of such couplers are Couplers (1) and (3) disclosed in U.S. Pat. No. 4,327,173, Compounds (3) and (16) disclosed in U.S. Pat. No. 4,564,586, Compounds (1) and (3) disclosed in U.S. Pat. No. 4,430,423, and the compounds illustrated below:

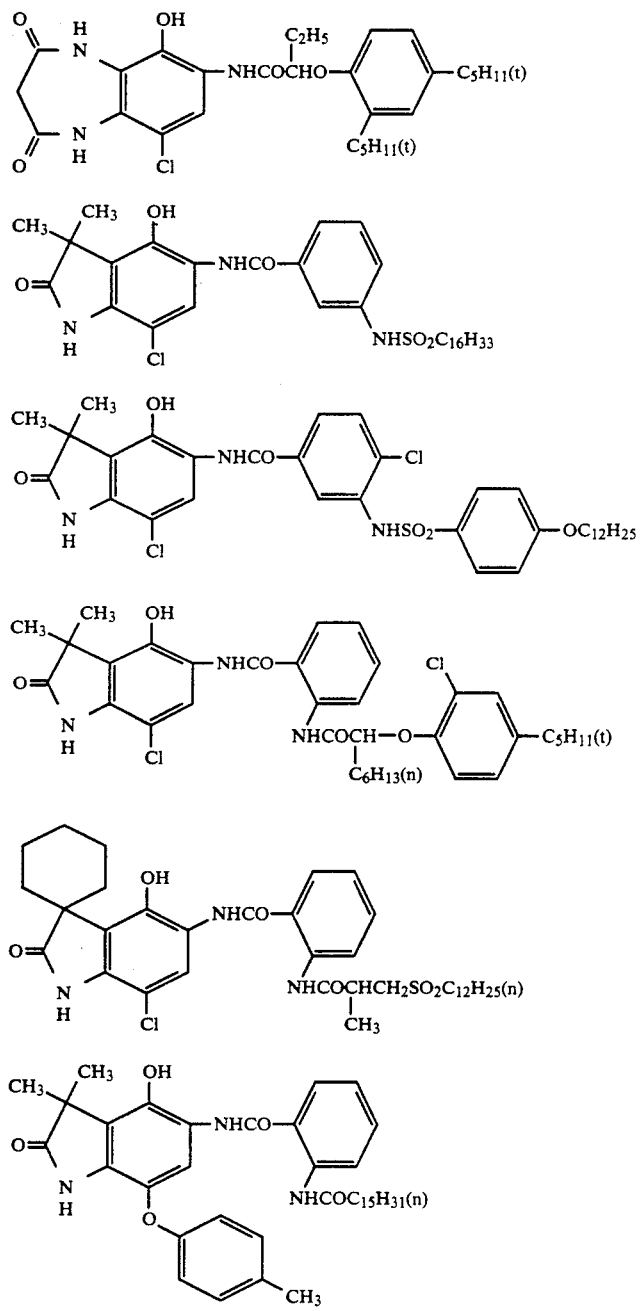

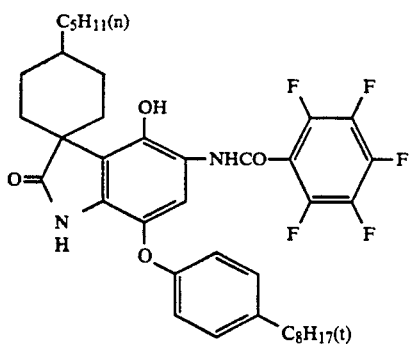
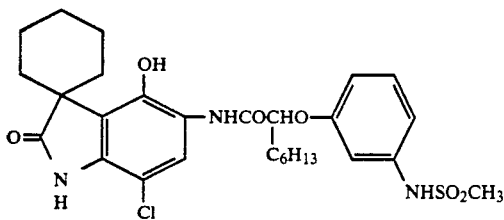
In addition to the above-mentioned types of cyan couplers, diphenylimidazole cyan couplers disclosed in EP-0249453-A2, specific examples of which are illustrated below, can also be employed in the present invention.
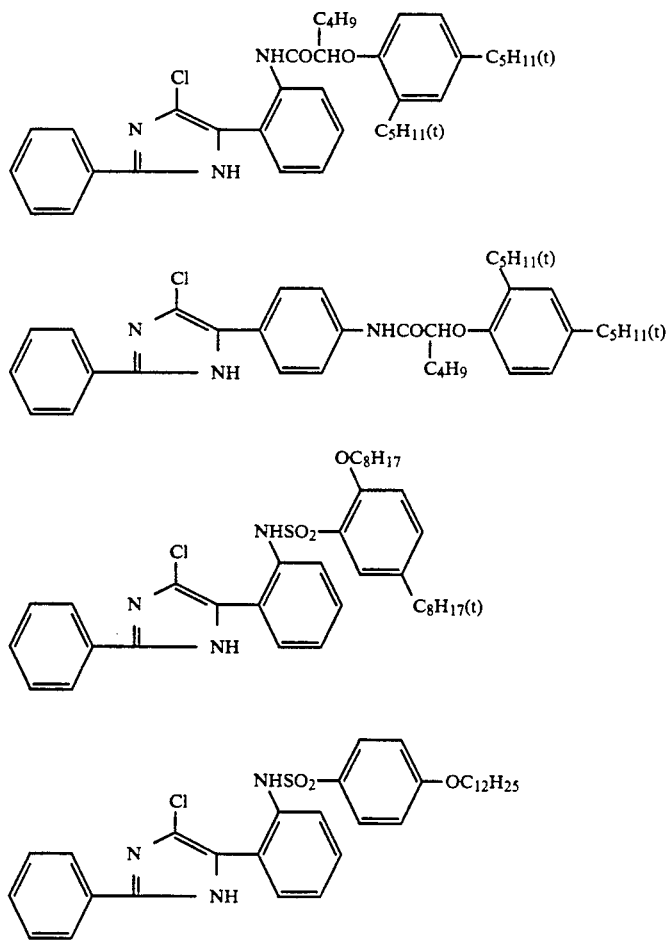

-continued

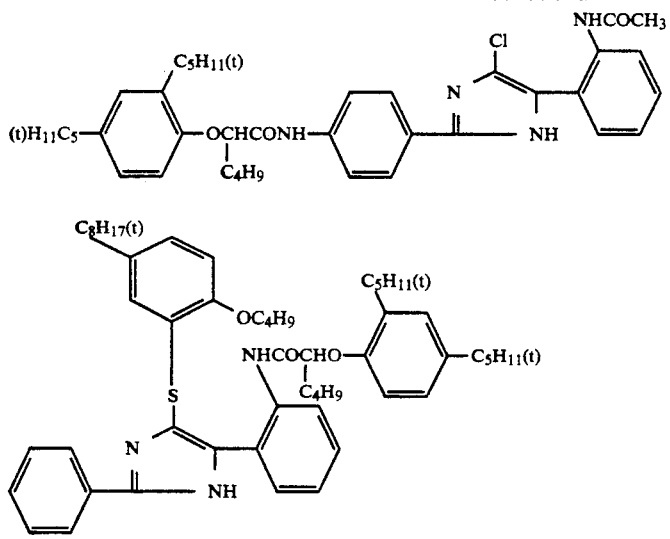

Further, ureido couplers disclosed in U.S. Pat. Nos. 4,333,999, 4,451,559, 4,444,872, 4,427,767 and 4,579,813, and EP-067689-B1 can be employed as a phenol cyan coupler. Representative examples of such couplers include Coupler (7) disclosed in U.S. Pat. No. 4,333,999, Coupler (1) disclosed in U.S. Pat. No. 4,451,559, Coupler (14) disclosed in U.S. Pat. No. 4,444,872, Coupler (3) disclosed in U.S. Pat. No. 4,427,767, Couplers (6) and (24) disclosed in U.S. Pat. No. 4,609,619, Couplers (1) and (11) disclosed in U.S. Pat. No. 4,579,813, Couplers (45) and (50) disclosed in EP-067689-B1, Coupler (3) disclosed in JP-A-61-42658, and so on.

As for the naphthol cyan couplers, those having an N-alkyl-N-arylcarbamoyl group at the 2-position of their respective naphthol nuclei (as disclosed, for instance, in U.S. Pat. No. 2,313,586), those having an alkylcarbamoyl group at the 2-position (as disclosed, for instance, in U.S. Pat. Nos. 2,474,293 and 4,282,312), those having an arylcarbamoyl group at the 2-position (as disclosed, for instance, in JP-B-50-14523; the term "JP-B" as used herein means an examined Japanese patent publication), those having a carbonamido or a sulfonamido group at the 2-position (as disclosed, for instance, in JP-A-60-237448, JP-A-61-145557, and JP-A-61-153640), those containing an aryloxy group as a eliminable group (as disclosed, for instance, in U.S. Pat. No. 3,476,563), those containing a substituted alkoxy group as a eliminable group (as disclosed, for instance, in U.S. Pat. No. 4,296,199), those containing a glycolic acid group as a eliminable group (as disclosed, for instance, in JP-B-60-39217), and so on can be used in the present invention.

The coupler of the present invention, and the above-illustrated cyan and yellow couplers are incorporated into their respective silver halide emulsion layers to be used in combination in an amount of preferably 0.1 to 1.0 mole, more preferably 0.1 to 0.5 mole, per mole of silver halide contained in each emulsion layer.

Each of these couplers can be incorporated into an emulsion layer in such a manner so that it is dispersed together with at least one high boiling organic solvent. High boiling organic solvents which can preferably be used therein are represented by the following general formulae (A) to (E):

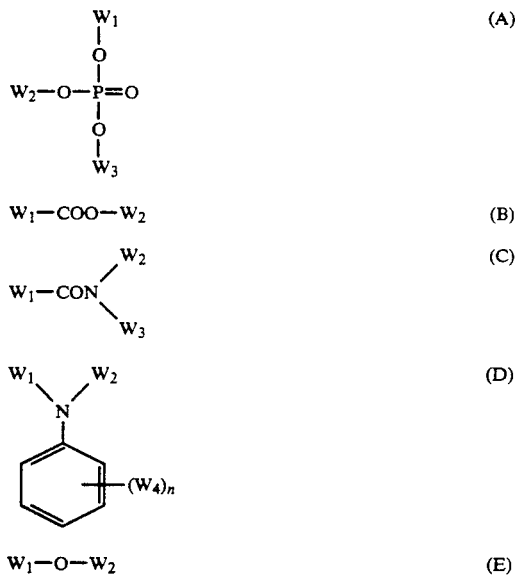

wherein $W_1$, $W_2$ and $W_3$ each represents a substituted or an unsubstituted alkyl, cycloalkyl, alkenyl, aryl or heterocyclyl group; $W_4$ represents $W_1$, $OW_1$, or $S\text{-}W_1$; n represents an integer of 1 to 5, and when n is 2 or more, the $W_4$'s may be the same or different; and in formula (E), a condensed ring may be formed by $W_1$ and $W_2$.

Details of these high boiling organic solvents are described in JP-A-62-215272, from the lower left column on page 137 to the upper right column on page 144. Other types of high boiling organic solvents which can be used effectively with the coupler of the present invention include N,N-dialkylaniline derivatives. Among such derivatives, those having an alkoxy group in the position ortho to the N,N-dialkylamino group are favored over the others. The following compound represents a specific example of such a derivative:

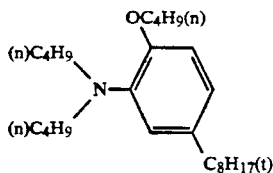

High boiling organic solvents of this type are advantageously used in preventing magenta stain from being produced in the white area of a color print with the passage of time after photographic processing, and in preventing the generation of fog due to development. These high boiling organic solvents are, in general, used in proportion of 10 to 500 mol%, preferably 20 to 300 mol%, to the coupler used.

Also, the above-described couplers can be impregnated into loadable latex polymers (as disclosed, for instance, in U.S. Pat. No. 4,203,716) in the presence or absence of the above-illustrated high boiling organic solvents, or the couplers can be dissolved in polymers insoluble in water and soluble in organic solvents, and then dispersed into aqueous solutions of hydrophilic colloids in the form of an emulsion.

Examples of such polymers, homopolymers or copolymers disclosed in World Patent WO 88/00723, pages 12 to 30, are preferably used. The use of acrylamide polymers are particularly preferable with respect to the stabilization of color images to be formed.

The photographic material produced in accordance with the present invention may contain as a color fog inhibitor a hydroquinone derivative, an aminophenol derivative, a gallic acid derivative, an ascorbic acid derivative, or the like.

Various kinds of discoloration inhibitors can be used in the photosensitive material of the present invention. Typical examples of organic discoloration inhibitors for cyan, magenta and/or yellow images include hindered phenols represented by hydroquinones, 6-hydroxychromans, 5-hydroxycoumarans, spirochromans, p-alkoxyphenols and bisphenols, gallic acid derivatives, methylenedioxybenzenes, aminophenols, hindered amines, and ether, or ester derivatives obtained by silylation or alkylation of phenolic hydroxy groups of the above compounds. In addition, metal complex salts represented by a (bis-salicylaldoximato)nickel complex and a (bis-N,N-dialkyldithiocarbamato)nickel complex can be employed as discoloration inhibitor.

Specific examples of organic discoloration inhibitors are described in the patents cited below. For instance, hydroquinones are disclosed, for example, in U.S. Pat. Nos. 2,360,290, 2,418,613, 2,700,453, 2,701,197, 2,728,659, 2,732,300, 2,735,765, 3,982,944 and 4,430,425, British Patent 1,363,921, U.S. Pat. Nos. 2,710,801 and 2,816,028, and so on; 6-hydroxychromans, 5-hydroxycoumarans and spirochromans are disclosed, for example, in U.S. Pat. Nos. 3,432,300, 3,573,050, 3,574,627, 3,698,909 and 3,764,337, JP-A-52-152225, and so on; spiroindanes are disclosed in U.S. Pat. No. 4,360,589; p-alkoxyphenols are disclosed, for example, in U.S. Pat. No. 2,735,765, British Patent 2,066,975, JP-A-59-10539, JP-B-57-19765 (the term "JP-B" as used herein means an examined Japanese patent publication), and so on; hindered phenols are disclosed, for example, in U.S. Pat. No. 3,700,455, JP A-52-72224, U.S. Pat. No. 4,228,235, JP-B-52-6623, and so on; gallic acid derivatives, methylenedioxybenzenes and aminophenols are disclosed, for example, in U.S. Pat. No. 3,457,079, U.S. Pat. No. 4,332,886 and JP-B-56-21144, respectively; hindered amines are disclosed, for example, in U.S. Pat. Nos. 3,336,135 and 4,268,593, British Patents 1,326,889, 1,354,313 and 1,410,846, JP-B-51-1420, JP-A-58-114036, JP-A-59-53846, JP-A-59-78344, and so on; ether and ester derivatives of phenolic hydroxy groups are disclosed, for example, in U.S. Pat. Nos. 4,155,765, 4,174,220, 4,254,216 and 4,264,720, JP-A-54-145530, JP-A-55-6321, JP-A-58-105147, JP-A-59-10539, JP-B-57-37856, U.S. Pat. No. 4,279,990, JP-B-53-3263, and so on; and metal complexes are disclosed, for example, in U.S. Pat. Nos. 4,050,938 and 4,241,155, British Patent 2,027,731(A), and so on. Each of these compounds can achieve its intended purpose by being emulsified together with a color coupler corresponding thereto in a proportion of 5 to 100 wt% to the color coupler, and then by being incorporated into a light-sensitive layer. In order to prevent a cyan dye image from undergoing deterioration by exposure to heat and light, especially light, it is more effective to introduce an ultraviolet absorbent into both layers adjacent to the cyan color-producing layer.

Among the above-cited discoloration inhibitors, the spiroindanes and the hindered amines are particularly preferred.

In the present invention, it is desirable that the compounds as described below should be used together with the above-described couplers, especially the pyrazoloazole couplers.

More specifically, for the purpose of preventing the generation of stain and other side reactions attributable to the production of developed dyes by the reaction between couplers and a color developer or the oxidation product thereof remaining in the film upon storage after photographic processing, it is desired that a compound (Q) capable of producing a chemically inert and substantially colorless compound by chemically binding to an aromatic amine color developing agent remaining after color development processings, and/or a compound (R) capable of producing a chemically inert and substantially colorless compound by chemically binding to the oxidation product of an aromatic amine color developing agent remaining after color development processings, should be used in combination, or independently.

Compounds preferred as compound (Q) include those undergoing a reaction with p-anisidine under such conditions that the rate constant in the second order reaction, $k_2$, should range from 1.0 l/mol·sec to $1 \times 10^{-5}$ l/mol·sec (in 80° C. trioctyl phosphate). The rate constant in the second order reaction can be measured using the method described in JP-A-63-158545.

When $k_2$ is greater than the above-defined range, the compounds themselves are unstable and frequently they decompose by a reaction with gelatin or water. On the other hand, when $k_2$ is smaller than the above-defined range, the reaction with the residual aromatic amine developing agent is slow. As a result of such a slow reaction, it frequently happens that the purpose of use of this compound, or the prevention of the side reaction of the residual aromatic amine developing agent cannot be achieved.

Compounds which are more preferred as compound (Q) can be represented by the following general formula (QI) or (QII):

$$R_1-(A)_n-X \quad \text{(QI)}$$

$$R_2-\underset{\underset{B}{|}}{C}=Y \quad \text{(QII)}$$

wherein $R_1$ and $R_2$ each represents an aliphatic group, an aryl group, or a heterocyclyl group; n represents 1 or 0; A represents a group capable of forming a chemical bond by reacting with an aromatic amine developing agent; X represents a group capable of splitting off by the reaction with an aromatic amine developing agent; B represents a hydrogen atom, an aliphatic group, an aryl group, a heterocyclyl group, an acyl group, or a sulfonyl group; and Y represents a group capable of accelerating the addition of an aromatic amine developing agent to the compound of general formula (QII); and further, $R_1$ and X, and Y and $R_2$ or B, respectively, may combine with each other to complete a cyclic structure.

The chemical binding to the residual aromatic amine developing agent can typically be effected through a substitution reaction or an addition reaction.

Specific examples of compounds represented by general formulae (QI) and (QII) are disclosed in JP A-63-158545, JP-A-62-283338, JP-A-64-2042 and JP-A-1-86139, and so on.

On the other hand, compounds which are more preferred as compound (R) capable of producing a chemically inert and colorless compound by chemically binding to the oxidation product of an aromatic amine color developing agent remaining after color development can be represented by the following general formula (RI):

$$R-Z \quad \text{(RI)}$$

wherein R represents an aliphatic group, an aromatic group or a heterocyclyl group; and Z represents a nucleophilic group, or a group capable of releasing a nucleophilic group through decomposition in the photosensitive material. Among the compounds represented by general formula (RI), those containing as Z a group whose Pearson's nucleophilicity $^nCH_3I$ value (R.G. Pearson, et al., J. Am. Chem. Soc., vol. 90, p. 319 (1968) is at least 5, or a group derived therefrom are favored.

Specific examples of compounds represented by general formula (RI) include those disclosed in European Patent (unexamined published) 255,722, JP-A-62-143048, JP-A-62-229145, JP-A-1-86139, Japanese Patent Application Nos. 63-136724, 62-214681 and 62-158342, and so on.

In addition, the details of combinations of the above-described compound (Q) and compound (R) are described in European Patent (unexamined published) 277589.

The photosensitive material of the present invention may contain water-soluble dyes in hydrophilic colloid layers as a filter dye, for prevention of irradiation or for other various purposes. Suitable examples of such dyes include oxonol dyes, hemioxonol dyes, styryl dyes, merocyanine dyes, cyanine dyes and azo dyes. Of these dyes, oxonol dyes, hemioxonol dyes and merocyanine dyes are more useful.

As a binder or a protective colloid for the emulsion layers of the photosensitive material of the present invention, gelatin is advantageously used. Also, hydrophilic colloids other than gelatin can be used alone or together with gelatin.

Gelatin used in the present invention may either be lime-processed or acid-processed. Details of the preparation of gelatin are described in Arthur Veis, The Macromolecular Chemistry of Gelatin, Academic Press (1964).

Supports which can be used in the present invention include transparent or reflecting supports generally used in photographic light-sensitive materials, such as cellulose nitrate film and polyethylene terephthalate film. Reflecting supports are more desirable in order to obtain the object of the present invention.

The term "reflecting support" as used in the present invention refers to a support which can enhance the reflectivity and contribute to the sharpness of a dye image formed in the silver halide emulsion layers, and includes support materials on which hydrophobic resins containing light-reflecting substances, such as titanium oxide, zinc oxide, calcium carbonate, calcium sulfate, etc., in a dispersed condition are coated, and films of hydrophobic resins in which light-reflecting substances are dispersed. Specific examples thereof include baryta paper, polyethylene-coated paper, synthetic paper of the polypropylene type, and reflecting layer-laminated or reflecting substance-containing transparent supports Suitable examples of such transparent supports include a glass plate, films of polyesters such as polyethylene terephthalate, cellulose triacetate, cellulose nitrate, etc., polyamide films, polycarbonate films, polystyrene films, vinyl chloride resin films, and so on. The support to be used can properly be chosen from among the above-cited supports depending upon the intended end-use of the photographic material of the present invention.

As for the light-reflecting substances to be used, it is desirable that white pigments should be thoroughly kneaded in the presence of a surfactant, and pigment grains wherein the surfaces of which have been treated with a di- to tetra-hydric alcohol should be used.

An occupied area rate (%) of fine-grained white pigment per specified unit area can be most typically determined by dividing the observed area into the neighboring unit areas of 6 $\mu$m×6 $\mu$m, and measuring an occupied area rate Ri (%) of the fine grains projected on each unit area. A variation coefficient of the occupied area rate (%) can be defined as a ratio of the standard deviation of Ri, represented by s, to the mean of Ri, represented by $\overline{R}$. The number of unit areas to be examined as the subject, represented by n, is preferably 6 or more. Accordingly, the variation coefficient $s/\overline{R}$ can be determined according to the following equation:

$$\sqrt{\frac{\sum_{i=1}^{n}(Ri-R)^2}{n-1}} \bigg/ \frac{\sum_{i=1}^{n}Ri}{n}$$

In the present invention, a variation coefficient of the occupied area rate (%) of the fine-grained pigment is preferably 0.15 or less, more preferably 0.12 or less. When the variation coefficient is 0.08 or less, a dispersed condition of the grains can be said to be substantially "uniform".

A color developer which can be used in the present invention contains a known aromatic primary amine developing agent. Examples of developing agents which can preferably be used are p-phenylenediamine derivatives, and representatives thereof are cited below. However, the invention should not be construed as being limited to these representative examples.

D-1: N,N-Diethyl-p-phenylenediamine
D-2: 2-Amino-5-diethylaminotoluene
D-3: 2-Amino-5-(N-ethyl-N-laurylamino)toluene
D-4: 4-[N-Ethyl-N-($\beta$-hydroxyethyl)amino]aniline
D-5: 2-Methyl-4-[N-ethyl-N-($\beta$-hydroxyethyl)amino]aniline
D-6: 4-Amino-3-methyl-N-ethyl-N-[$\beta$-(methanesulfonamido)ethyl]aniline
D-7: N-(2-Amino-5-diethylaminophenylethyl)methanesulfonamido
D-8: N,N-Dimethyl-p-phenylenediamine
D-9: 4-Amino-3-methyl-N-ethyl-N-methoxyethylaniline
D-10: 4-Amino-3-methyl-N-ethyl-N-8-ethoxyethylaniline
D-11: 4-Amino-3-methyl-N-ethyl-N-8-butoxyethylaniline Of the above-cited p-phenylenediamine derivatives, 4-amino-3-methyl-N-ethyl-N-[$\beta$-(methanesulfonamido)ethyl]aniline (exemplified compound D-6) is particularly preferred over the others.

These p-phenylenediamine derivatives may assume the form of a salt, such as sulfate, hydrochloride, sulfite, p-toluenesulfonate, and so on. A preferred amount of the aromatic primary amine developing agent added to 1 liter of a developer ranges from about 0.1 g to about 20 g, particularly from about 0.5 g to about 10 g.

Moreover, a sulfite such as sodium sulfite, potassium sulfite, sodium hydrogen sulfite, potassium hydrogen sulfite, sodium metasulfite, potassium metasulfite, etc., or a carbonyl/sulfinic acid adduct can be added to the color developer, if desired. However, in the case when benzyl alcohol is excluded in order to reduce the environmental pollution load, or so on, it is advantageous with respect to color developability that the color developer does not contain, in a substantial sense, sulfite ion. The effect of the present invention is remarkable in particular in the above-described case. The expression "does not contain in a substantial sense" means that the sulfite ion concentration in the color developer is below 0.5 g/l, preferably below 0.2 g/l, and more preferably zero, calculated as sodium sulfite.

In addition, it is desirable that various kinds of hydroxylamines, hydroxamic acids disclosed in JP-A-63-43138, hydrazines and hydrizides disclosed in Japanese Patent Application No. 61-170756, phenols disclosed in JP-A-63-44657 and JP-A-63-58443, α-hydroxyketones and α-aminoketones disclosed in JP-A-63-44656, and/or various kinds of sugars disclosed in JP-A-63-36244 should be added for the purpose of directly preserving the above-described color developing agents. Moreover, the combined use of the above-described compounds with monoamines as disclosed in Japanese Patent Application No. 61-164515, JP-A 63-4235, JP-A-63-24254, JP-A-63-21647, JP-A-63-27841 and JP-A-63 25654, diamines as disclosed in Japanese Patent Application No. 61-164515, JP-A-63-30845 and JP-A-63-43139, polyamines as disclosed in JP-A-63-21647 and JP-A-63-26655, polyamines disclosed in JP-A-63-44655, nitroxy radicals disclosed in JP-A-63-53551, alcohols as disclosed in JP-A-63-43140 and JP-A-63-53549, oximes as disclosed in JP-A-63-56654, and/or tertiary amines as disclosed in Japanese Patent Application No. 61-265149 is advantageous.

Other preservative for the developer include various metals disclosed in JP-A 57-44148 and JP-A-57-53749, salicylic acids disclosed in JP-A-59-180588, alkanolamines disclosed in JP-A-54-3532, polyethyleneimines disclosed in JP-A-56-94349, aromatic polyhydroxy compounds disclosed in U.S. Pat. No. 3,746,544, and so on, if desired. In particular, the addition of alkanolamines such as triethanolamine, dialkylhyroxylamines such as diethylhydroxylamine, or aromatic polyhydroxy compounds, is preferred.

The color developer to be used in the present invention is preferably adjusted to pH 9 to 12, more preferably pH 9 to 11.0. In addition to the above-described ingredients, the color developer can contain other known compounds as developer components.

For the purpose of maintaining the foregoing pH, it is desirable that various kinds of buffering agents be used. Specific examples of suitable buffering agents include carbonates, phosphates, tetraborates, hydroxybenzoates, glycyl salts, N,N,-dimethylglycine salts, leucine salts, norleucine salts, guanine salts, 3,4-dihydroxyphenylaniline salts, alanine salts, aminobutyric acid salts, 1-amino-2-methyl-1,3-propanediol salts, valine salts, proline salts, trishyhydroxyaminomethane salts, lysine salts, and the like. Among these buffering agents, carbonates, phosphates, tetraborates and hydroxybenzoates are particularly preferred, because they have a high solubility, an excellent buffering ability in a high pH region beyond pH 9.0, no adverse effect upon the photographic properties (e.g., generation of fog) when added to a color developer, and they are available at a low cost.

Specific examples of the above-cited buffering agents include sodium carbonate, potassium carbonate, sodium hydrogen carbonate, potassium hydrogen carbonate, trisodium phosphate, tripotassium phosphate, disodium phosphate, dipotassium phosphate, sodium borate, potassium borate, sodium tetraborate (borax), potassium tetraborate, sodium o-hydroxybenzoate (sodium salicylate), potassium o-hydroxybenzoate, sodium 5-sulfo-2-hydroxybenzoate (sodium 5-sulfosalicylate), potassium 5-sulfo-2-hydroxybenzoate (potassium 5-sulfosalicylate), and so on. However, the present invention should not be construed as being limited to these compounds.

An amount of the buffering agents to be added to the color developer is preferably 0.1 mol/l or more, and particularly in the range from 0.1 to 0.4 mol/l.

In addition, various kinds of chelating agents can be contained in the color developer in order to prevent calcium and magnesium from precipitating, or in order to enhance the stability of the color developer.

Specific examples of chelating agents which can be used include nitrilotriacetic acid, diethylenetriaminepentaacetic acid, ethylenediaminetetraacetic acid, N,N,N-trimethylenephosphonic acid, ethylenediamine-N,N,N',N'-tetramethylenephosphonic acid, trans-cyclohexanediaminetetraacetic acid, 1,2-diaminopropanetetraacetic acid, glycoletherdiaminetetraacetic acid, ethylenediamine-o-hydroxyphenylacetic acid, 2-phosphonobutane-1,2,4-tricarboxylic acid, 1-hydroxyethylidene-1,1-diphosphonic acid, and N,N,'-bis(2-hydroxybenzyl)ethylenediamine-N,N'-diacetic acid.

These chelating agents may be used in combination of two or more thereof, if desired.

When these chelating agents are added in an amount sufficient enough to mask the metal ions in the color developer, they can serve the intended purpose. For instance, they may be added in an amount of 0.1 to 10 g per liter of the color developer.

The color developer can contain any development accelerator, if desired. As a typical color development accelerator, benzyl alcohol can be used. However, it is desirable with respect to a reduction in pollution load, ease of preparation and prevention of color stain that the color developer to be used in the present invention does not contain benzyl alcohol in a substantial sense. The expression "in a substantial sense" as used herein means that the color developer may contain benzyl alcohol in a concentration of 2 ml/l or less, and preferably it does not contain benzyl alcohol at all.

Other development accelerators that can be optionally added include thioether compounds as disclosed in JP-B-37-16088, JP-B-37-5987, JP-B-38-7826, JP-B-44-12380, JP-B-45-9019 and U.S. Pat. No. 3,813,247, p-phenylenediamine compounds as disclosed in JP-A-52-49829 and JP-A-50-15554, quaternary ammonium salts as disclosed in JP-A-50-137726, JP-B-44-30074, JP-A-56-156826 and JP-A-52-43429, amine compounds as disclosed in U.S. Pat. Nos. 2,494,903, 3,128,182, 4,230,793 and 3,253,919, JP-B-41-11431, and U.S. Pat. Nos. 2,482,546, 2,596,926, and 3,582,346 polyalkyleneoxides as disclosed in JP-B-37-16088, JP-B-42-25201, U.S. Pat. No. 3,128,183, JP-B-41-11431, JP-B-42-23883 and U.S. Pat. No. 3,532,501, 1-phenyl-3-pyrazolidones, imidazoles and so on.

The color developer to be used in the present invention can contain any antifoggant, if desired. Suitable examples of antifoggants which can be used include alkali metal halides such as sodium chloride, potassium bromide and potassium iodide, and organic antifoggants. Typical examples of organic antifoggants include nitrogen-containing heterocyclic compounds such as benzotriazole, 6-nitrobenzimidazole, 5-nitroisoindazole, 5-methylbenzotriazole, 5-nitrobenzotrizole, 5-chlorobenzotriazole, 2-thiazolyl-benzimidazole, 2-thiazolyl-methyl-benzimidazole, indazole, hydroxyazaindolizine, and adenine.

Further, the color developer to be used in the present invention preferably contains a brightening agent. Suitable brightening agents are 4,4'-diamino-2,2'-disulfostilbene compounds, and a preferred amount thereof to be added is in the range from 0 to 5 g/l, particularly from 0.1 to 4 g/l.

Furthermore, the color developer may contain various kinds of surface active agents such as alkylsulfonic acids, arylsulfonic acids, aliphatic carboxylic acids and aromatic carboxylic acids, if desired.

The process using the color developer of the present invention is performed at a temperature ranging from 20° C. to 50° C., preferably from 30° C. to 40° C. The processing time ranges from 20 seconds to 5 minutes, preferably from 30 seconds to 2 minutes. It is desirable that a replenisher be added in a rather small amount, and the amount ranges from 20 to 600 ml, preferably from 50 to 300 ml, more preferably from 60 ml to 200 ml, and most preferably from 60 ml to 150 ml per square meter of the sensitive material to be processed.

A desilvering step performed in the present invention is described in detail below.

In general, desilvering may be effected by any step, for example, by a combined step of bleach and fixation, by a combined step of fixation and blix, by a combined step of bleach and blix, by a step of blix, and so on.

A bleaching bath, a bleach-fix bath and a fixing bath which can be used in the present invention are described below.

In a bleaching bath or a bleach-fix bath to be used in the present invention, although any bleaching agent can be used, the organic complex salts of iron(III) (e.g., Fe(III) complex salts of aminopolycarboxylic acids, such as ethylenediaminetetraacetic acid, diethylenetriaminepentaacetic acid, etc., aminopolyphosphonic acids, phosphonocarboxylic acids, organic phosphonic acids), organic acids such as citric acid, tartaric acid, malic acid, and so on), persulfates, hydrogen peroxide, and the like are used to a great advantage.

Of these bleaching agents, organic complex salts of Fe(III) are particularly preferred over the others with respect to rapid processing and prevention of environmental pollution. Examples of aminopolycarboxylic acids, aminopolyphosphonic acids, organic phosphonic acids and salts thereof which are useful for forming the organic complex salts of Fe(III) include ethylenediaminetetraacetic acid, diethylenetriaminepentaacetic acid, 1,3-diaminopropanetetraacetic acid, propylenediaminetetraacetic acid, nitrilotriacetic acid, cyclohexanediaminetetraacetic acid, methyliminodiacetic acid, iminodiacetic acid, glycoletherdiaminetetraacetic acid, and so on. These compounds may assume the form of a sodium, potassium, lithium or ammonium salt. Of these bleaching agents, (ethylenediaminetetraacetato)iron(III), (diethylenetriaminepentaacetato)iron(III), (cyclohexanediaminetetraacetato)iron(III), (1,3diaminopropanetetraacetato)iron(III) and (methyliminodiacetato)iron(III) complexes are preferred over the others because of their high bleaching power.

These ferric ion complexes may be used in the form of a complex salt, or they may be formed in a solution by using ferric salts, such as ferric sulfates, ferric chloride, ferric nitrate, ammonium ferric sulfate, ferric phosphate, etc., and chelating agents of an aminopolycarboxylic acid, aminopolyphosphonic acid, phosphonocarboxylic acid, etc. Moreover, these chelating agents may be used in excess of the amounts required for forming the ferric ion complexes. Preferred ferric ion complexes are ferric complexes of aminopolycarboxylic acids, and a suitable amount of these complexes added is in the range from 0.01 to 1.0 mole, preferably from 0.05 to 0.50 mole, per liter of the solution.

The bleaching bath, bleach-fix bath and/or the pre-bath thereof can contain various kinds of compounds as a bleach accelerator. Examples of bleach accelerators which are preferred with respect to a great accelerating effect include the compounds containing a mercapto group or a disulfide linkage, as described in U.S. Pat. No. 3,893,858, German Patent 1,290,812, JP-A-53-95630 and Research Disclosure, No. 17129 (July 1978), thiourea compounds as disclosed in JP-B-45-8506, JP-A-52-20832, JP-A-53-32735 and U.S. Pat. No. 3,706,561, and halogen ions such as iodine and bromide ions.

In addition, the bleaching or the bleach-fix bath used in the present invention can contain rehalogenating agents such as bromides (e.g., potassium bromide, sodium bromide, ammonium bromide), chlorides (e.g., potassium chloride, sodium chloride, ammonium chloride), or iodides (e.g., ammonium iodide). Further, the bleaching or the bleach-fix bath can contain one or more inorganic or organic acids, an alkali metal or ammonium salt thereof which has a pH buffering ability, such as borax, sodium metaborate, acetic acid, sodium acetate, sodium carbonate, potassium carbonate, phosphorous acid, phosphoric acid, sodium phosphate, citric acid, sodium citrate, tartaric acid, etc., and a corrosion inhibitor such as ammonium nitrate, guanidine, etc.

Fixing agents which can preferably be used in the bleach-fix bath or the fixing bath used in the present invention include known ones, that is, water-soluble silver halide solvents, such as thiosulfates (e.g., sodium thiosulfate, ammonium thiosulfate, etc.); thiocyanates (e.g., sodium thiocyanate, ammonium thiocyanate, etc.); thioether compounds (e.g., ethylenebisthioglycolic acid, 3,6-dithia-1,8-octanediol, etc.); thioureas; and so on. These silver halide solvents can be used alone or as a mixture of two or more thereof. Also, a special bleach-fix bath which contains, for instance, a combination of the fixing agent disclosed in JP-A-55-155354 with a large amount of halide such as potassium iodide, can be employed. In the present invention, it is desirable that a thiosulfate, especially ammonium thiosulfate, should be used as the fixing agent. The amount of the fixing agent which is added ranges from 0.3 to 2 moles, preferably from 0.5 to 1.0 mole, per liter of the bath. The bleach-fix and fixing bath of the present invention are adjusted to preferably pH 3 to 10, more preferably pH 5 to 9.

The bleach-fix bath can contain various kinds of brightening agents, defoaming agents, surface active agents, polyvinyl pyrrolidone, and organic solvents such as methanol, and so on.

The bleach-fix and fixing baths used in the present invention can contain as preservative a sulfinic acid ion-releasing compounds, such as sulfites (e.g., sodium sulfite, potassium sulfite, ammonium sulfite) hydrogen sulfites (e.g., ammonium hydrogen sulfite, sodium hydrogen sulfite, potassium hydrogen sulfite), metabisulfites (e.g., potassium metabisulfite, sodium metabisulfite, ammonium metabisulfite), etc. These presevative compounds are preferably added in an amount of about 0.02 to 0.50 mol/l, particularly 0.04 to 0.40 mol/l, calculated as the sulfinic acid ion.

Although sulfites are generally used as the preservative, other preservatives such as ascorbic acid, adducts of carbonyl compounds and bisulfites, carbonyl compounds and so on may be added.

Further, buffering agents, brightening agents, chelating agents, defoaming agents, antimold compounds, and so on may optionally be added.

After the desilvering step, such as the fixing or the blix step, the silver halide color photographic material of the present invention is, in general, subjected to a washing step and/or a stabilizing step.

The volume of the washing water required can be determined depending on the characteristics of the photosensitive materials to be processed (e.g., on what types of couplers are incorporated therein), on the intended end-use of the photosensitive materials to be processed, on the temperature of washing water, on the number of washing tanks (e.g., stage number), in the manner of replenishing the washing water (e.g., as to whether the current of the water flows in the counter direction, or not), and on other various conditions. Of these conditions, the relationship between the number of washing tanks and the volume of washing water in the multistage counter-current process can be determined according to the methods described in *Journal of the Society of Motion Picture and Television Engineers*, volume 64, pages 248 to 253 (May 1955). A preferred number of steps in the multistage counter-current process is generally from 2 to 6, particularly from 2 to 4.

According to the multistage counter-current process, the volume of the washing water can be sharply reduced. For instant, it becomes feasible to decrease the washing water to 0.5 to 1 liter or less per square meters of the sensitive material processed. The remarkable effects of the present invention can be obtained in such a manner. However, the process has disadvantages, for example, because bacteria propagate themselves in the tanks as a result of an increase in the period of time that the water remains in the tanks, so that a suspended matter produced from the bacteria sticks to the photosensitive materials processed therein. In the processing of the color photosensitive material of the present invention, the method of reducing the content of calcium and magnesium, which is disclosed in JP-A-62-288838, can be employed to a great advantage as the means of solving the above-described problem. Further, bactericides that can be used in the present invention include isothiazolone compounds and thiabendazole disclosed in JP-A-57-8542, chlorine-containing germicides such as a sodium salt of chlorinated isocyanuric acid disclosed in JP-A-61-120145, benzotriazoles disclosed in JP-A-61-267761, and copper ion. Other germicides that can be used in the present invention include those described in Hiroshi Horiguchi *Bohkin Bohbai Zai no Kagaku* (which means "Chemistry of Antibacteria and Antimolds"), *Biseibutsu no Mekkin Sakkin Bohbi Gijutsu* (which means "Art of Sterilizing and Pasteurizing Microbe and Proofing Against Mold"), compiled by Eisei Gijutsu Kai, and *Bohkin- and Bohbai-zai Jiten* (which means "Theseaurus of Antibacteria and Antimolds"), compiled by Nippon Bohkin Bohbai Gakkai.

In addition, the washing water can contain a surface active agent as a draining agent, and a chelating agent such as EDTA as a water softener.

Subsequent to the above-described washing step, or without using any washing step, the photosensitive material of the present invention is processed with a stabilizing bath. To the stabilizing bath are added compounds having an image-stabilizing function, such as aldehyde compounds represented by formaldehyde, buffering compounds for adjusting the film pH to a value suitable for stabilization of the produced dyes, and ammonium compounds. In addition, the stabilizing bath can contain the above-described various kinds of bactericides and antimold compounds for the purpose of preventing the propagation of bacteria in the bath, and for imparting an antimold capability to the sensitive materials processed thereby.

Further, surface active agents, brightening agents and hardeners can be added to the stabilizing bath.

When the sensitive material of the present invention is directly subjected to the stabilization step without using any washing step, all known methods, as described in JP-A-57-8543, JP-A-58-14834, JP-A-60-220345 and so on can be applied to the stabilization step.

Also, a desirable embodiment of the present invention is the addition of chelating agents such as 1-hydroxyethylinene-1,1-diphosphonic acid, ethylenediaminetetramethylenephosphonic acid, etc., magnesium compounds and bismuth compounds.

Moreover, in the present invention, the so-called rinsing solutions can be used as the washing water or as the stabilizing solution used after the desilvering step.

The washing step or the stabilization step in the present invention is preferably carried out at pH 4 to 10, more preferably pH 5 to 8. The processing temperature can be variously chosen depending on the characteristics and the intended use of the photosensitive material to be processed. The processing temperature is generally in the range of 15° C. to 45° C., preferably 20° C. to 40° C. The processing time, although it can be arbitrarily chosen, is preferably short in order to reduce the processing time. Specifically, a processing time from 15 sec. to 1 min. and 45 sec., especially from 30 sec. to 1 min. and 30 sec., is advantageously employed.

In addition, using a replenisher in a smaller amount is more desirable from the viewpoint of operating cost, reduction in the amount of waste, ease in handling, and so on. Specifically, a preferred replenishing amount is 0.5 to 50 times, preferably 3 to 40 times, as much as the amount of the processing solution carried from the pre-bath by the per unit area of photosensitive material. More specifically, the amount of replenisher is below 1 liter, especially below 500 ml, per $m^2$ of the photosensitive material. The replenishment may be carried out continuously or intermittently.

Solution(s) used in the washing and/or the stabilization step can be further used in a previous step. For instance, the wash water overflowing the washing bath, which is reduced in volume by using a multistage counter current process, is conducted into the prebath, that is, the bleach-fix bath, and the bleach-fix bath is replenished with a concentrated solution to achieve the reduction of waste solutions.

The combined time of the desilvering, washing and stabilizing steps in the present invention is below 2 min., preferably from 30 sec. to 1 min. and 30 sec. The term "combined time" as used herein refers to the time from the contact of the silver halide color photographic material with the first bath in the desilvering step until the material leaves the last bath in the washing or stabilizing step, and it is intended to include the intervals for the transportation of the material from one bath to another.

The foregoing expression "combined time of the desilvering, washing and stabilizing steps is below 2 min" signifies that the sum of the desilvering time and the time spent in the steps carried out before the drying step (namely, washing and/or stabilizing step) is below 2 min., and more specifically (1) the sum of the desilvering and the washing times, (2) the sum of the desilvering and the stabilizing times, or (3) the sum of the desilvering, the washing and the stabilizing times is below 2 min.

The present invention will now be illustrated in more detail by reference to the following examples.

EXAMPLE 1

To 10.0 g of a comparative magenta coupler having the structural formula (E×M-1) illustrated below were added 6.7 ml of tri(2-ethylhexyl)phosphate, 12.3 ml of tricresyl phosphate and 25 ml of ethyl acetate. The mixture was made into a solution by heating, then admixed with 100 ml of an aqueous solution containing 10 g of gelatin and 1.0 g of sodium dodecylbenzenesulfonate, and heated at a high temperature while stirring to obtain a fine emulsion. This emulsion was admixed with 100 g of silver chlorobromide emulsion having a silver bromide content of 80 mol% (containing 6.5 g of silver), and 10 ml of 2% aqueous solution of 2,4-dihydroxy-6-chloro-s-triazine-sodium salt as a hardener was added thereto. The thus obtained composition was coated at a silver coverage of 200 mg/$m^2$ on a paper support laminated with polyethylene on both sides, and a gelatin layer was further provided as the upper layer of this coating to prepare a sample.

Other photosensitive materials were prepared in the same manner as described above, except the magenta couplers of the present invention set forth in Table 1 and the other comparative magenta coupler (E×M-2) illustrated below were used instead of said magenta coupler, respectively.

Each of these photosensitive materials was subjected to wedgewise exposure of 1,000 cms, and then these materials were processed as described below.

The photographic characteristics of these photosensitive materials were evaluated by the measurements of minimum density (Dmin), maximum density (Dmax) and gradation. The gradation was expressed in terms of the slope of a straight line connecting a point corresponding to the density of 0.5 to another point corresponding to the density of 1.5 on each characteristic curve.

In addition, the evaluation of hue was made by measuring a reflection spectrum at the spot having a magenta density of 1.0, determining a half width of the spectrum, and expressing it as a relative value with the magenta coupler (ExM-1) being taken as 100. The half width was determined using the method described in *Bunseki Kaqaku Hanno no Kiso* (which means "fundamentals of analytical chemical reactions"), edited by the Hokkaido branch of The Analytical Chemical Society of Japan and published by Baihukan. When the half width of the spectrum is narrower, the magenta coupler produces a better hue.

Comparative Magenta Coupler (ExM-1)

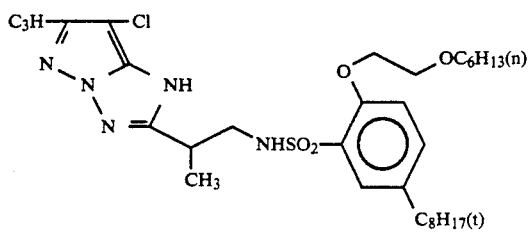

Comparative Magenta Coupler (ExM-1)

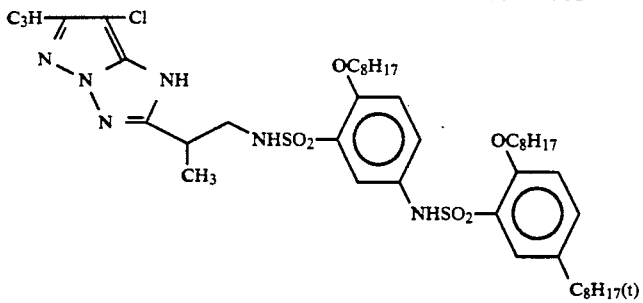

-continued

| Processing Step | Temperature | Time |
| --- | --- | --- |
| Color development | 37° C. | 3 min. 30 sec. |
| Bleach-Fix | 33° C. | 1 min. 30 sec. |
| Washing | 24 to 34° C. | 3 min. |
| Drying | 70 to 80° C. | 1 min. |

The compositions of the processing solutions used were as follows.

| Color Developer: | |
| --- | --- |
| Water | 800 ml |
| Diethylenetriaminepentaacetic acid | 1.0 g |
| Nitrilotriacetic acid | 2.0 g |
| Benzyl alcohol | 15 ml |
| Diethylene glycol | 10 ml |
| Sodium sulfite | 2.0 g |
| Potassium bromide | 1.0 g |
| Potassium carbonate | 30 g |
| N-Ethyl-N-($\beta$-methanesulfonamidoethyl)-3-methyl-4-aminoaniline sulfate | 4.5 g |
| Hydroxylamine sulfate | 3.0 g |
| Brightening agent (WHITEX 4B, produced by Sumitomo Chemical Co., Ltd.) | 1.0 g |
| Water to make | 1,000 ml |
| pH (at 25° C.) | 10.25 |
| Bleach-fix Bath: | |
| Water | 400 ml |
| Ammonium thiosulfate (700 g/l) | 150 ml |
| Sodium sulfite | 18 g |
| Ammonium ethylenediaminetetraacetatoferrate (III) | 55 g |
| Disodium ethylenediaminetetraacetate | 5 g |
| Water to make | 1,000 ml |
| pH (at 25° C.) | 6.70 |

TABLE 1

| Sensitive Material | Magenta Coupler | Photographic Characteristics | | | Half Width | Note |
| --- | --- | --- | --- | --- | --- | --- |
| | | Dmin | Dmax | Gradation | | |
| A | ExM-1 | 0.12 | 2.79 | 2.80 | 100 | Comparison |
| B | ExM-2 | 0.12 | 2.82 | 2.81 | 98 | Comparison |
| C | M-1 | 0.12 | 2.88 | 2.92 | 87 | Invention |
| D | M-2 | 0.11 | 2.87 | 2.89 | 88 | Invention |
| E | M-3 | 0.12 | 2.86 | 2.88 | 88 | Invention |
| F | M-5 | 0.11 | 2.87 | 2.87 | 89 | Invention |
| G | M-6 | 0.12 | 2.86 | 2.86 | 88 | Invention |
| H | M-4 | 0.12 | 2.84 | 2.85 | 88 | Invention |
| I | M-13 | 0.12 | 2.87 | 2.89 | 88 | Invention |
| J | M-14 | 0.12 | 2.86 | 2.88 | 87 | Invention |
| K | M-15 | 0.11 | 2.86 | 2.86 | 84 | Invention |
| L | M-16 | 0.12 | 2.86 | 2.85 | 82 | Invention |
| M | M-19 | 0.12 | 2.97 | 3.00 | 87 | Invention |

As can be seen from Table 1, all of the couplers of the present invention have a narrow half width, that is to say, showed excellent hue, and at the same time have excellent color formability (high Dmax and low Dmin). In addition, the dyes produced therefrom have a sharp absorption, especially with a sharply cut tail on the longer wavelength side, so that they were desirable for color reproduction.

EXAMPLE 2

On a paper support laminated with polyethylene on both sides thereof was coated the layers described below in this order to prepare a multilayer color photographic paper. The coating compositions were prepared in the following manner.

Preparation of Coating Composition for First Layer 27.2 ml of ethyl acetate, 4.1 g of a solvent (Solv-3) and 4.1 g of a solvent (Solv-6) were added to a mixture of 19.1 g of a yellow coupler (ExY), 4.4 g of a color image stabilizer (Cpd-1) and 1.8 g of a color image stabilizer (Cpd-7) to make a solution. The solution was emulsified and dispersed in 185 ml of a 10% aqueous gelatin solution containing 8 ml of a 10% sodium dodecylbenzenesulfonate solution. On the other hand, a silver chlorobromide emulsion (having a silver bromide content of 80.0 mol%, a crystal form of a cube, an average grain size of 0.85 μm and a variation coefficient of 0.08) and a silver chlorobromide emulsion (having a bromide content of 80.0%, a crystal form of a cube, an average grain size of 0.62 μm and a variation coefficient of 0.07) were mixed in a ratio of 1:3 (by mole on silver basis), subjected to sulfur sensitization, and admixed with $5.0 \times 10^{-4}$ mol/mol Ag of the blue-sensitive sensitizing dye illustrated below. The thus prepared emulsion and the foregoing emulsified dispersion were mixed homogeneously, and further the composition was adjusted so that the resulting emulsion has the composition described below. Thus, the coating composition for the first layer was prepared. The coating compositions for the second to the seventh layers were prepared in a similar manner as that for the first layer. In each layer, a sodium salt of 1-oxy-3,5-dichloro-s-triazine was contained as a gelatin hardener.

The spectral sensitizing dyes illustrated below were used in the light-sensitive layers corresponding thereto, respectively.

To the blue-sensitive emulsion layer, the green-sensitive emulsion layer and the red-sensitive emulsion layer, were further added 1-)5-methyl-ureidophenyl)-5-mercaptotetrazole in the amounts of $4.0 \times 10^{-6}$ mole, $3.0 \times 10^{-5}$ mole and $1.0 \times 10^{-5}$ mole, respectively, per mole of silver halide, and 2-methyl-5-t-octylhydroquinone in the amounts of $8 \times 10^{-3}$ mole, $2 \times 10^{-2}$ mole and $2 \times 10^{-2}$ mole, respectively, per mole of silver halide.

To the blue-sensitive emulsion layer and the green-sensitive emulsion layer, were further added 4-hydroxy-6-methyl-1,3,3a,7-tetrazaindene in the amounts of $1.2 \times 10^{-2}$ mole and $1.1 \times 10^{-2}$ mole, respectively, per mole of silver halide.

In addition, in order to prevent irradiation, the dyes illustrated below were added to each emulsion layer:

Blue-sensitive Emulsion Layer

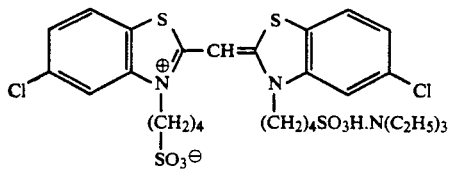

($5.0 \times 10^{-4}$ mole per mole of silver halide)

Green-sensitive Emulsion Layer

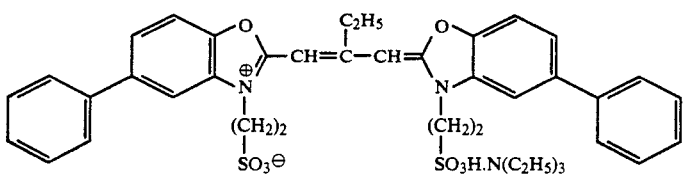

($4.0 \times 10^{-4}$ mole per mole of silver halide)

and

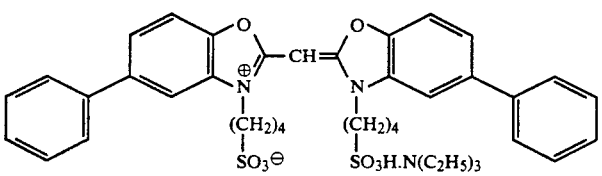

($7.0 \times 10^{-5}$ mole per mole of silver halide)

Red-sensitive Emulsion Layer

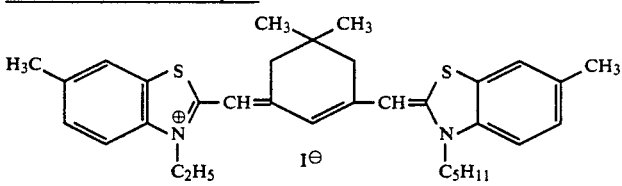

($0.9 \times 10^{-4}$ mole per mole of silver halide)

The compound illustrated below was further added to the red-sensitive emulsion layer in an amount of $2.6 \times 10^{-3}$ mole per mole of silver halide:

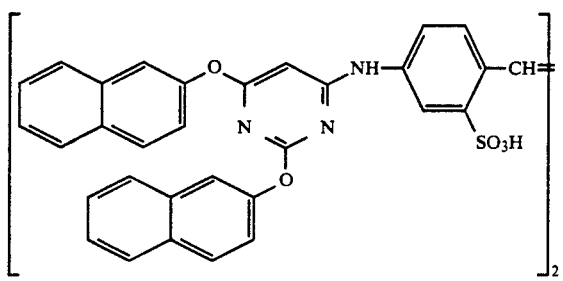

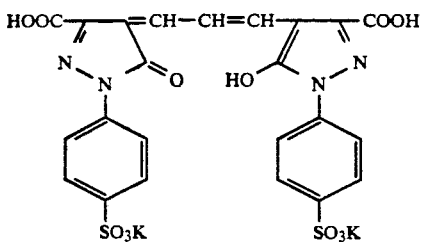

and

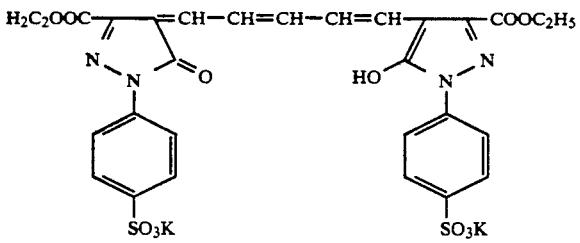

Layer Constituent

The ingredients used and their coverages are expressed in terms of g/m² as described below. Moreover, only the coverage of the silver halide is expressed on a silver bases.

| Support | |
|---|---|
| Polyethylene-laminated paper (containing a white pigment (TiO₂) and a bluish dye (ultramarine) on the first layer side). | |
| First Layer (Blue-sensitive layer) | |
| Silver chlorobromide emulsion described above (silver bromide content: 80 mol %) | 0.26 |
| Gelatin | 1.83 |
| Yellow coupler (ExY) | 0.83 |
| Color image stabilizer (Cpd-1) | 0.19 |
| Color image stabilizer (Cpd 7) | 0.08 |
| Solvent (Solv-3) | 0.18 |
| Solvent (Solv-6) | 0.18 |
| Second Layer (Color mixing inhibiting layer) | |
| Gelatin | 0.99 |
| Color mixing inhibitor (Cpd-6) | 0.08 |
| Solvent (Solv-1) | 0.16 |
| Solvent (Solv-4) | 0.18 |
| Third Layer (Green-sensitive layer): | |
| 1:1 (by mole on silver basis) Mixture of silver chlorobromide emulsion (silver bromide content: 90 mol %, crystal form: cube, average grain size: 0.47 μm, variation coefficient: 0.12) and silver chlorobromide emulsion (silver bromide content: 90 mol %, crystal form: cube, average grain size: 0.36 μm, variation coefficient: 0.09) | 0.16 |
| Gelatin | 1.79 |
| Magenta coupler (ExM-1) | 0.22 |
| Color image stabilizer (Cpd-3) | 0.20 |
| Color image stabilizer (Cpd-8) | 0.03 |
| Color image stabilizer (Cpd-4) | 0.01 |
| Color image stabilizer (Cpd-9) | 0.04 |
| Solvent (Solv-2) | 0.65 |
| Fourth Layer (Ultraviolet absorbing layer) | |
| Gelatin | 1.58 |
| Ultraviolet absorbent (UV-1) | 0.47 |
| Color mixing inhibitor (Cpd-5) | 0.05 |
| Solvent (Solv-5) | 0.24 |
| Fifth Layer (Red-sensitive layer) | |
| 1:2 (by mole on silver basis) Mixture of silver chlorobromide emulsion (silver bromide content: 70 mol %, crystal form: cube, average grain size: 0.49 μm, variation coefficient: 0.08) and silver chlorobromide emulsion (silver bromide content: 70 mol %, crystal form: cube, average grain size: 0.34 μm, variation coefficient: 0.10) | 0.23 |
| Gelatin | 1.34 |
| Cyan coupler (ExC) | 0.30 |
| Color image stabilizer (Cpd-6) | 0.17 |
| Color image stabilizer (Cpd-7) | 0.40 |
| Solvent (Solv-6) | 0.20 |
| Sixth Layer (Ultraviolet absorbing layer) | |
| Gelatin | 0.53 |
| Ultraviolet absorbent (UV-1) | 0.16 |
| Color mixing inhibitor (Cpd-5) | 0.02 |
| Solvent (Solv-5) | 0.08 |
| Seventh Layer (Protective layer) | |
| Gelatin | 1.33 |
| Acryl modified copolymer of polyvinyl alcohol (modification degree: 17%) | 0.17 |
| Liquid paraffin | 0.03 |

(Cpd-1) Color image stabilizer

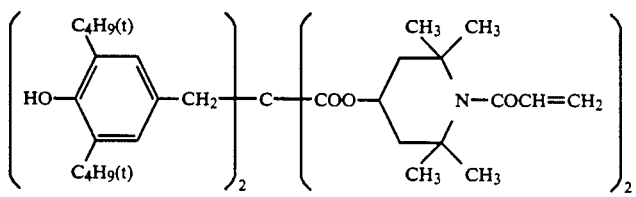

(Cpd-3) Color image stabilizer

-continued
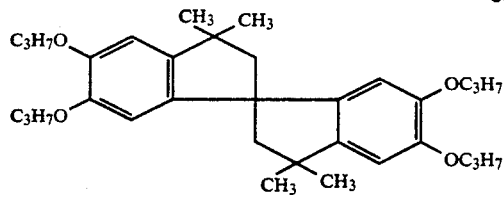
(Cpd-4) Color image stabilizer
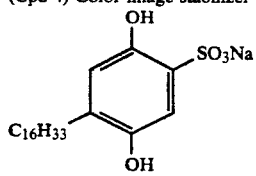
(Cpd-5) Color mixing inhibitor
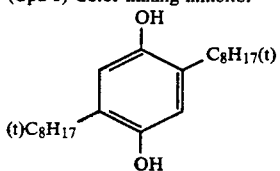
(Cpd-6) Color image stabilizer
2:4:4 (by weight) Mixture of:
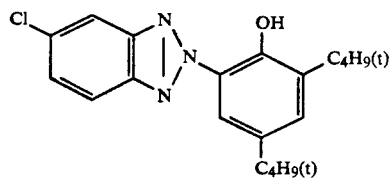
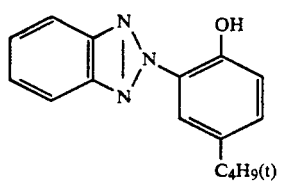
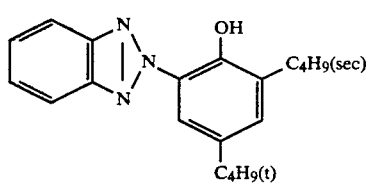
(Cpd-7) Color image stabilizer
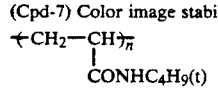
(Cpd-8) Color image stabilizer
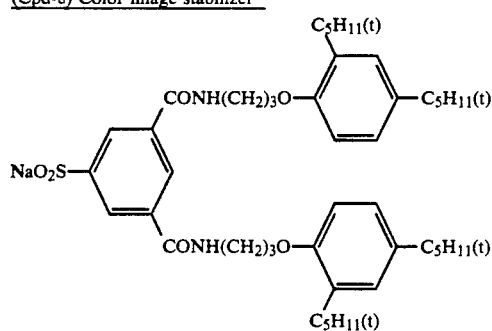

(Cpd-9) Color image stabilizer
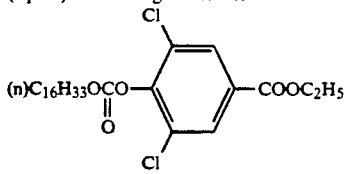
(UV-1) Ultraviolet absorbent
4:2:4 (by weight) Mixture of:
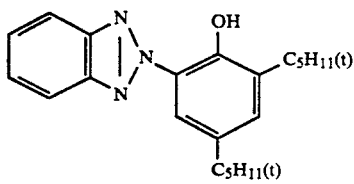
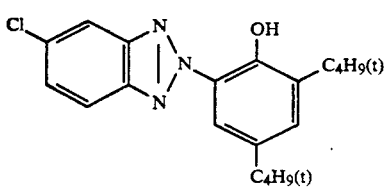
and
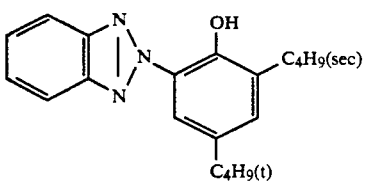
(Solv-1) Solvent
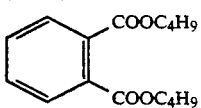
(Solv-2) Solvent
2:1 (by weight) Mixture of
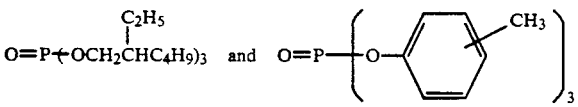
(Solv-3) Solvent
O=P(̵O—C$_9$H$_{19}$-(iso))$_3$
(Solv-4) Solvent
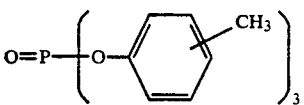
(Solv-5) Solvent
COOC$_9$H$_{17}$
|
(CH$_2$)$_8$
|
COOC$_8$H$_{17}$
(Solv-6) Solvent
C$_8$H$_{17}$CHCH(CH$_2$)$_7$COOC$_8$H$_{17}$
\ /
O
(ExY) Yellow coupler -continued

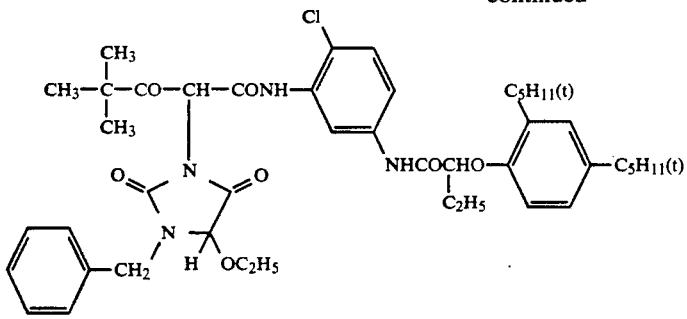

(ExM-1) Magenta coupler

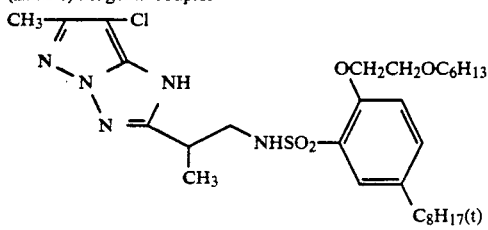

(ExC) Cyan coupler
1:1 (by mole) Mixture of

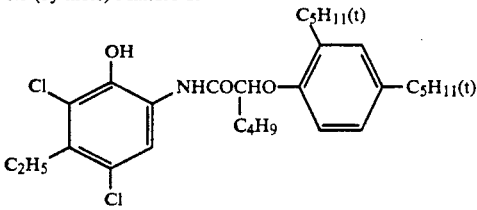

and

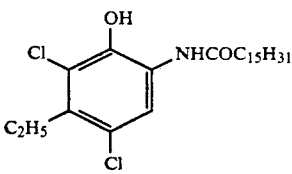

Then, the other photosensitive materials were prepared in the same manner as described above, except that the magenta coupler in the third layer (green-sensitive layer) was replaced by equimolar amounts of the magenta couplers set forth in Table 2, respectively.

The above-described samples were each subjected to wedgewise exposure through three-color separation filters for sensitometry use by means of a sensitometer (FWH model made by Fuji Photo Film Co., Ltd. with light source color temperature of 3200°K). The exposure was performed so that an exposure of 250 CMS was given to each sample with an exposure time of 0.1 sec.

The thus exposed samples were each subjected to photographic processing having the following steps using the processing solutions containing the compositions described below, respectively. An automatic developing machine was used for the photographic processing.

| Processing Step | Temperature | Time |
|---|---|---|
| Color Development | 37° C. | 3 min. 30 sec. |
| Bleach-Fix | 33° C. | 1 min. 30 sec. |
| Washing | 24 to 34° C. | 3 min. |

| Processing Step | Temperature | Time |
|---|---|---|
| Drying | 70 to 80° C. | 1 min. |

The compositions of the processing solutions were as follows.

| Color Developer: | |
|---|---|
| Water | 800 ml |
| Diethylenetriaminepentaacetic acid | 1.0 g |
| Nitrilotriacetic acid | 2.0 g |
| Benzyl alcohol | 15 ml |
| Diethylene glycol | 10 ml |
| Sodium sulfite | 2.0 g |
| Potassium bromide | 1.0 g |
| Potassium carbonate | 30 g |
| N-Ethyl-N-(β-methanesulfonamidoethyl)-3-methyl-4-aminoaniline sulfate | 4.5 g |
| Hydroxylamine sulfate | 3.0 g |
| Brightening agent (WHITEX 4B, produced by Sumitomo Chemical Co., Ltd.) | 1.5 g |
| Water to make | 1,000 ml |
| pH (at 25° C.) | 10.25 |
| Bleach-fix Bath: | |
| Water | 400 ml |
| Ammonium thiosulfate (700 g/l) | 150 ml |

| -continued | |
|---|---|
| Sodium sulfite | 18 g |
| Ammonium ethylenediaminetetra-acetatoferrate (III) | 55 g |
| Disodium ethylenediaminetetra-acetate | 5 g |
| Water to make | 1,000 ml |
| pH (at 25° C.) | 6.70 |

The photographic characteristics and the hue of the green-sensitive layers were evaluated using the same measurements as in Example 1.

Simultaneously with these measurements, the magenta reflection densities in the unexposed areas (stain) were measured. Thereafter, the sensitive materials were allowed to stand for 10 days at 60° C., 70% RH. The stain densities were then measured again, and the sensitive materials were thus examined for increments of stain.

The results obtained are shown in Table 2.

TABLE 2

| Sensitive Material | Magenta Coupler | Photographic Characteristics | | | Half Width | Increase in Stain after Processing | Note |
|---|---|---|---|---|---|---|---|
| | | Dmin | Dmax | Gradation | | | |
| A | ExM-1 | 0.11 | 2.12 | 2.67 | 100 | +0.12 | Comparison |
| B | ExM-3 | 0.12 | 2.02 | 2.51 | 100 | +0.10 | Comparison |
| C | M-1 | 0.12 | 2.24 | 2.74 | 87 | +0.06 | Invention |
| D | M-2 | 0.11 | 2.26 | 2.76 | 88 | +0.05 | Invention |
| E | M-4 | 0.12 | 2.26 | 2.73 | 88 | +0.06 | Invention |
| F | M-14 | 0.11 | 2.26 | 2.77 | 87 | +0.04 | Invention |
| G | M-8 | 0.12 | 2.26 | 2.72 | 87 | +0.04 | Invention |
| H | M-6 | 0.12 | 2.25 | 2.71 | 88 | +0.05 | Invention |

Comparative Magenta Coupler (ExM-3)

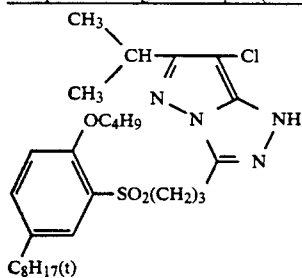

As can be seen from the data in Table 2, every compound of the present invention demonstrated excellent hue and high color formability compared with the comparative compounds, and an increase of stain after processing was depressed in every sample of the present invention. Accordingly, stain was not generated in the white background with the passage of time, which was advantageous with respect to image quality.

EXAMPLE 3

On a paper support laminated with polyethylene on both sides thereof was coated the layers described below in this order to prepare a multilayer color photographic paper. The coating compositions were prepared in the following manner.

Preparation of Coating Composition for First Layer

To 19.1 g of a yellow coupler (ExY), 4.4 g of a color image stabilizer (Cpd-1) and 0.7 g of a color image stabilizer (Cpd-7) were added 27.2 ml of ethyl acetate and 8.2 g of a solvent (Solv-3) to make a solution. The solution was emulsified and dispersed in 185 ml of a 10% aqueous gelatin solution containing 8 ml of a 10% sodium dodecylbenzenesulfonate solution. On the other hand, a silver chlorobromide emulsion (having a crystal form of a cube, an average grain size of 0.88 μm and a variation coefficient of 0.08) and a silver chlorobromide emulsion (having a crystal form of a cube, an average grain size of 0.70 μm and a variation coefficient of 0.10), each have 0.2 mol% of silver bromide contained therein in such a manner so as to be localized at the grain surface. The blue-sensitive sensitizing dyes illustrated below were added to the former emulsion in an amount of $2.0 \times 10^{-4}$ mole per mole of silver, while to the latter oemulsion the foregoing blue-sensitive sensitizing dyes were added in an amount of $2.5 \times 10^{-4}$ mole per mole of silver, were mixed in a ratio of 3:7 (by mole on a silver basis), and then subjected to sulfur sensitization. The thus prepared emulsion and the foregoing emulsified dispersion were mixed homogeneously to prepare the coating composition shown hereinafter for the first layer. The coating compositions for the second to the seventh layers were prepared in a similar manner to that for the first layer. In each layer, a sodium salt of 1-oxy-3,5-dichloro-s-triazine was contained as gelatin hardener.

The spectral sensitizing dyes illustrated below were used in the light-sensitive layers corresponding thereto, respectively.

Blue-sensitive Emulsion Layer

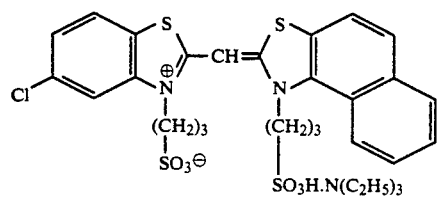

-continued

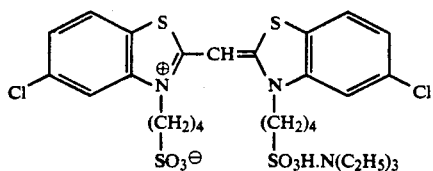

(Each was added in an amount of $2.0 \times 10^{-4}$ mol/mol Ag to the large-size emulsion, and in an amount of $2.5 \times 10^{-4}$ mol/mol Ag to the small-size emulsion).

Green-sensitive Emulsion Layer

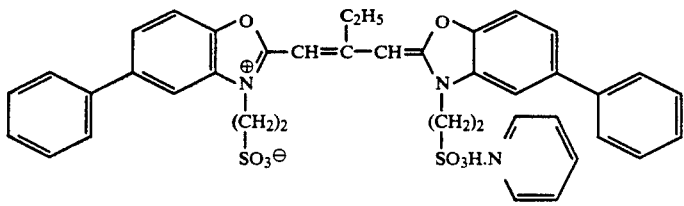

($4.0 \times 10^{-4}$ mol/mol Ag to the large-size emulsion, and $5.6 \times 10^{-4}$ mol/mol Ag to the small-size emulsion)

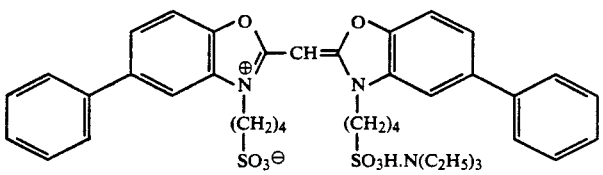

($7.0 \times 10^{-5}$ mol/mol Ag to the large-size emulsion, and $1.0 \times 10^{-5}$ mol/mol Ag to the small-size emulsion)

Red-sensitive Emulsion Layer

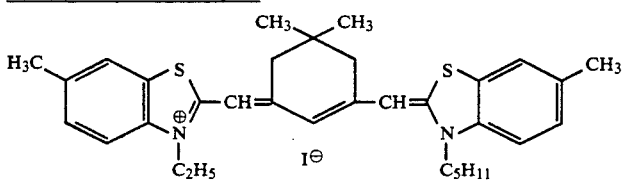

($0.9 \times 10^{-4}$ mol/mol Ag to the large-size emulsion, and $1.1 \times 10^{-4}$ mol/mol Ag to the smal-size emulsion)

The compound illustrated below was further added to the red-sensitive emulsion layer in an amount of $2.6 \times 10^{-3}$ mole per mole of silver halide:

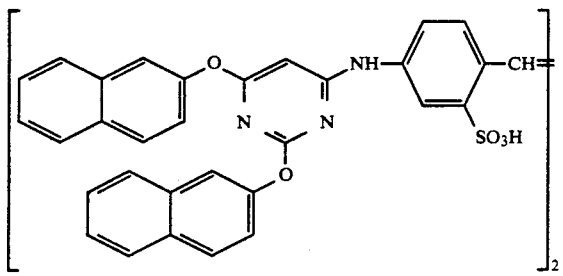

To the blue-sensitive emulsion layer, the green-sensitive emulsion layer and the red-sensitive emulsion layer were further added 1-(5-methyl-ureidophenyl)-5-mercaptotetrazole in the amounts of $8.5 \times 10^{-5}$ mole, $7.7 \times 10^{-4}$ mole and $2.5 \times 10^{-4}$ mole, respectively, per mole of silver halide.

Moreover, in order to prevent irradiation, the dyes illustrated below were added to each emulsion layer:

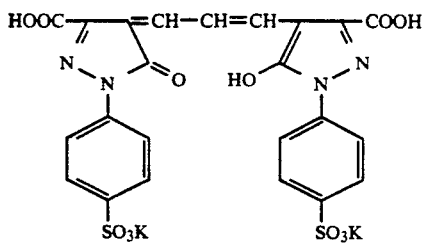

and

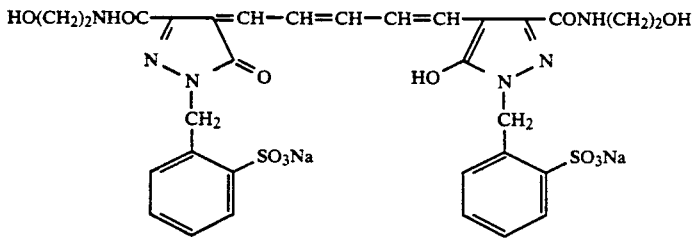

Constituent Layers

The ingredients used in each layer and their coverages are expressed in terms of g/m² as described below. In addition, only the coverage of the silver halide is expressed on a silver basis.

| Support | |
|---|---|
| Polyethylene-laminated paper (containing a white pigment (TiO₂) and a bluish dye (ultramarine) on the first layer side). | |
| First Layer (Blue-sensitive layer) | |
| Silver chlorobromide emulsion described above | 0.30 |
| Gelatin | 1.86 |
| Yellow coupler (ExY) | 0.82 |
| Color image stabilizer (Cpd-1) | 0.19 |
| Solvent (Solv-3) | 0.35 |
| Color image stabilizer (Cpd-7) | 0.06 |
| Second Layer (Color stain inhibiting layer) | |
| Gelatin | 0.99 |
| Color mixing inhibitor (Cpd-5) | 0.08 |
| Solvent (Solv-1) | 0.16 |
| Solvent (Solv-4) | 0.18 |
| Third Layer (Green-sensitive layer): | |
| 1:3 (by mole on silver basis) Mixture of silver chlorobromide emulsion (crystal form: cube, average grain size: 0.55 μm, variation coefficient: 0.10) and silver chlorobromide emulsion (crystal form: cube, average grain size: 0.39 μm, variation coefficient: 0.08), in each of which 0.8 mol % of AgBr was localized at the grain surface | 0.12 |
| Gelatin | 1.24 |
| Magenta coupler (ExM-4) | 0.14 |
| Color image stabilizer (Cpd-3) | 0.15 |
| Color image stabilizer (Cpd-4) | 0.02 |
| Color image stabilizer (Cpd-2) | 0.03 |
| Color image stabilizer (Dpd-9) | 0.02 |
| Solvent (Solv-2) | 0.40 |
| Fourth Layer (Ultraviolet absorbing layer) | |
| Gelatin | 1.58 |
| Ultraviolet absorbent (UV-1) | 0.47 |
| Color mixing inhibitor (Cpd-5) | 0.05 |
| Solvent (Solv-5) | 0.24 |
| Fifth Layer (Red-sensitive layer) | |
| 1:4 (by mole on silver basis) Mixture of silver chlorobromide emulsion (crystal form: cube, average grain size: 0.58 μm, variation coefficient: 0.09) and silver chlorobromide emulsion (crystal form: cube, average grain size: 0.45 μm, variation coefficient: 0.11), in each of which 0.6 mol % of AgBr was localized at the grain surface | 0.23 |
| Gelatin | 1.34 |
| Cyan coupler (ExC) | 0.32 |
| Color image stabilizer (Cpd-6) | 0.17 |
| Color image stabilizer (Cpd-8) | 0.04 |
| Color image stabilizer (Cpd-7) | 0.40 |
| Solvent (Solv-6) | 0.15 |
| Sixth Layer (Ultraviolet absorbing layer) | |
| Gelatin | 0.53 |
| Ultraviolet absorbent (UV-1) | 0.16 |
| Color mixing inhibitor (Cpd-5) | 0.02 |
| Solvent (Solv-5) | 0.08 |
| Seventh Layer (Protective layer) | |
| Gelatin | 1.33 |
| Acryl modified copolymer of polyvinyl alcohol (modification degree: 17%) | 0.17 |
| Liquid paraffin | 0.03 |

(ExY) Yellow

-continued
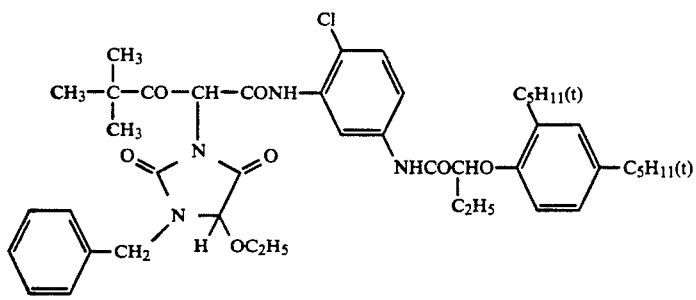
(ExM-1) Magenta coupler
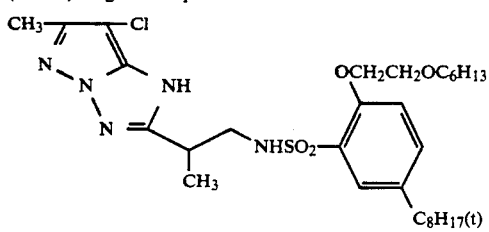
(ExM-4) Magenta coupler
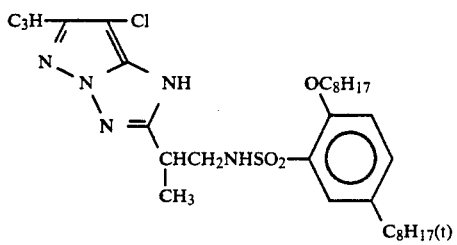
(ExC) Cyan coupler
2:4:4 (by weight) Mixture of
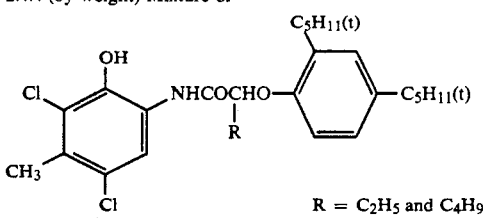
R = $C_2H_5$ and $C_4H_9$
and
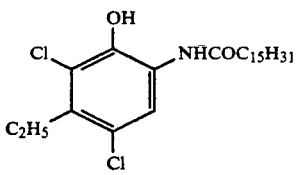
(Cpd-1) Color image stabilizer
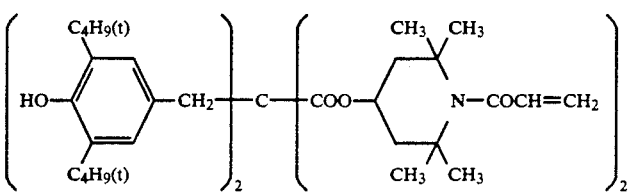
(Cpd-2) Color image stabilizer

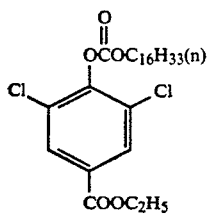
(Cpd-3) Color image stabilizer
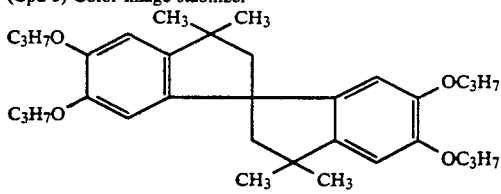
(Cpd-4) Color image stabilizer
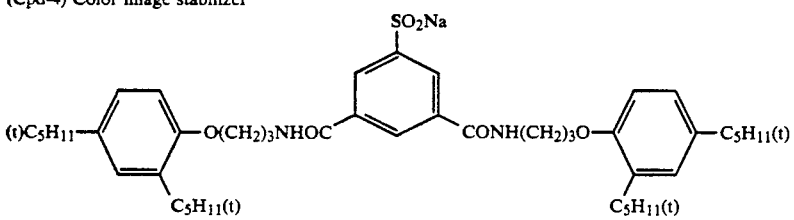
(Cpd-5) Color mixing inhibitor
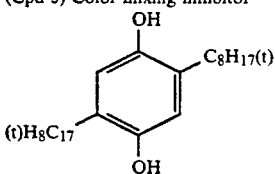
(Cpd-6) Color image stabilizer
2:4:4 (by weight) Mixture of
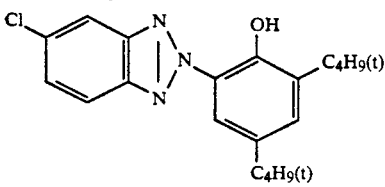
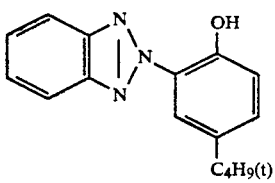
and
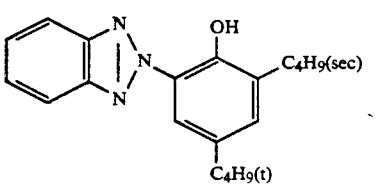
(Cpd-7) Color image stabilizer
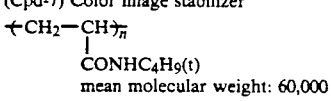
mean molecular weight: 60,000

(Cpd-8) Color image stabilizer
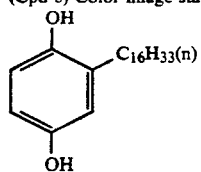
(Cpd-9) Color image stabilizer
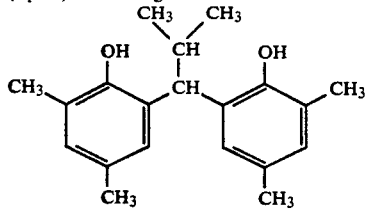
(UV-1) Ultraviolet absorbent
4:2:4 (by weight) Mixture of
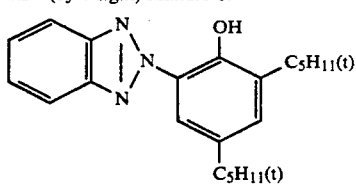
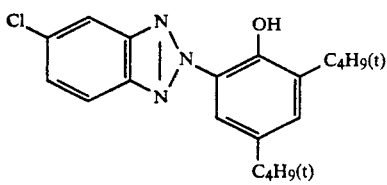
and
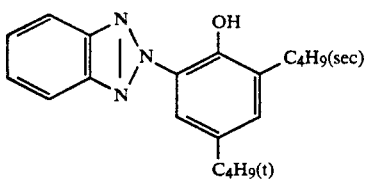
(Solv-1) Solvent
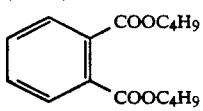
(Solv-2) Solvent
2:1 (by volume) Mixture of
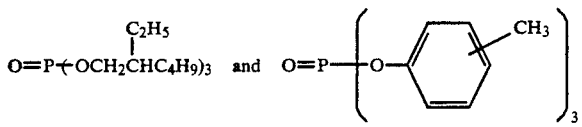
(Solv-3) Solvent
$O=P(\!\!+\!\!O-C_9H_{19}\text{-(iso)})_3$
(Solv-4) Solvent
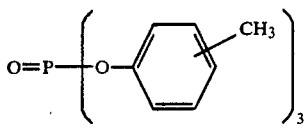

(Solv-5) Solvent

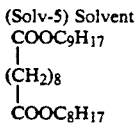

(Solv-6) Solvent

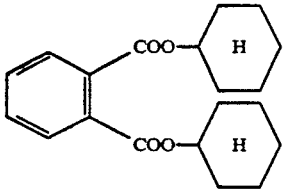

The other photosensitive materials were prepared in the same manner as described above, except that the magenta coupler in the third layer (green-sensitive layer) was replaced by equimolar amounts of the magenta couplers set forth in Table 3, respectively.

Each photosensitive material was exposed according to the method described in Example 2, and then subjected to running processing in a paper processing machine which included the following steps. The running processing was continued until the color developer was replenished to twice as much as the tank volume.

The photographic characteristics and stain were evaluated using the same methods as in Example 2.

| Processing step | Temperature | Time | Amount Replenished* | Tank Volume |
|---|---|---|---|---|
| Color Development | 38° C. | 45 sec. | 109 ml | 4 l |
| Bleach-Fix | 30° to 36° C. | 45 sec. | 215 ml | 4 l |
| Rinsing (1) | 30° to 37° C. | 20 sec. | — | 2 l |
| Rinsing (2) | 30° to 37° C. | 20 sec. | — | 2 l |
| Rinsing (3) | 30° to 37° C. | 20 sec. | 364 ml | 2 l |
| Drying | 70° to 80° C. | 60 sec. | | |

*per 1 m² of the light-sensitive material processed.

The replenishment of the rinsing solution was performed in the direction from the rinsing tank (3) to the rinsing tank (I) according to a three-tank counter-current replenishing process.

The compositions of the processing solutions used were as follows.

| | Tank Solution | Replenisher |
|---|---|---|
| Color Developer | | |
| Water | 800 ml | 800 ml |
| Ethylenediamine-N,N,N',N'-tetra-methylenephosphonic acid | 5.0 g | 5.0 g |
| 5,6-Dihydroxybenzene-2,4-disulfonic acid | 0.3 g | 0.3 g |
| Triethanolamine | 8.0 g | 8.0 g |
| Sodium chloride | 3.14 g | 0.0 g |
| Potassium bromide | 0.015 g | 0.0 g |
| Potassium carbonate | 25 g | 25 g |
| N-Ethyl-N-(β-methanesulfon-amidoethyl)-3-methyl-4-amino-aniline sulfate | 5.0 g | 9.5 g |
| N,N-bis(carboxymethyl)hydrazine | 0.03 mol | 0.05 mol |
| Sodium sulfite | 0.1 g | 0.2 g |
| Brightening agent (of diamino-stilbene type, WHITEX-4, produced by Sumitomo Chemical Co. Ltd.) | 1.0 g | 2.5 g |
| Water to make | 1,000 ml | 1,000 ml |
| pH (at 25° C.) | 10.05 | 10.60 |
| Bleach-fix Bath (Tank solution = Replenisher) | | |
| Water | 400 ml | |
| Ammonium thiosulfate (700 g/l) | 100 ml | |
| Sodium sulfite | 17 g | |
| Ammonium ethylenediaminetetra-acetatoferrate (III) | 55 g | |
| Disodium ethylenediaminetetra-acetate dihydrate | 5 g | |
| Ammonium bromide | 30 g | |
| Glacial acetic acid | 9 g | |
| Water to make | 1,000 ml | |
| pH (at 25° C.) | 5.40 | |
| Rinsing Solution (Tank solution = Replenisher) | | |
| Ion exchange water (in which calcium and magnesium ion concentrations were each below 3 ppm) | | |

TABLE 3

| Sensitive Material | Magenta Coupler | Photographic Characteristics | | | | | | Increase in Stain after Processing | Note |
|---|---|---|---|---|---|---|---|---|---|
| | | Fresh Solution | | | Running Solution | | | | |
| | | Dmin | Dmax | Gradation | Dmin | Dmax | Gradation | | |
| A | ExM-1 | 0.11 | 2.28 | 2.78 | 0.13 | 2.19 | 2.61 | +0.06 | Comparison |
| B | ExM-4 | 0.12 | 2.19 | 2.79 | 0.14 | 2.02 | 2.58 | +0.06 | Comparison |
| C | M-1 | 0.12 | 2.30 | 2.82 | 0.12 | 2.26 | 2.79 | +0.02 | Invention |
| D | M-2 | 0.12 | 2.31 | 2.83 | 0.11 | 2.27 | 2.79 | +0.01 | Invention |
| E | M-10 | 0.12 | 2.31 | 2.82 | 0.12 | 2.27 | 2.76 | +0.01 | Invention |
| F | M-15 | 0.12 | 2.32 | 2.81 | 0.12 | 2.29 | 2.77 | +0.02 | Invention |
| G | M-17 | 0.12 | 2.31 | 2.82 | 0.12 | 2.30 | 2.77 | +0.02 | Invention |
| H | M-19 | 0.11 | 2.31 | 2.82 | 0.12 | 2.29 | 2.77 | +0.01 | Invention |

As can be seen from the data shown in Table 3, the couplers of the present invention caused slight differences in the photographic characteristics between the case of using fresh processing solutions and the case of using running solutions, and considerably depressed any increase in the stain density with the passage of time after processing.

In addition, the compounds of the present invention produced dyes excellent in hue.

EFFECTS OF THE INVENTION

Accordingly, from the data obtained by the foregoing examples, the magenta couplers of the present invention have proved to have excellent hue and sufficiently high color formability. In addition, the couplers of the present invention have a rather low molecular weight and are easily synthesized, so that the production cost thereof is inexpensive. These features are greatly advantageous for the wide application of the couplers of the present invention to color photographic materials.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material, which comprises a support having thereon at least one silver halide emulsion layer, at least one of said emulsion layers containing at least one nondiffusible pyrazolo(1,5 b)(1,2,4)triazole magenta coupler represented by the following general formula (I):

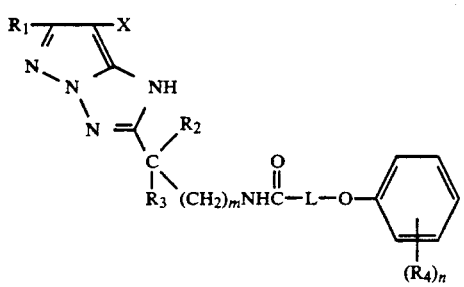
(I)

wherein $R_1$ represents an alkyl group; $R_2$ and $R_3$ each represents a hydrogen atom or an alkyl group, provided that both are not a hydrogen atom; $R_4$ represents an alkyl group, an alkoxy group or a halogen atom; L represents an alkylene group; m represents an integer of 0 to 5; n represents an integer of 0 to 5, and when n is 2 or more, the $R_4$'s may be different from one another; and X represents a halogen atom.

2. The silver halide color photographic material of claim 1, wherein $R_1$ is a straight or a branched chain, or a cyclic unsubstituted alkyl group containing 1 to 10 carbon atoms.

3. The silver halide color photographic material of claim 1, wherein $R_2$ and $R_3$ each represents a straight or branched chain unsubstituted alkyl group containing 1 to 10 carbon atoms.

4. The silver halide color photographic material of claim 1, wherein $R_4$ is a straight or a branched chain, or a cycloalkyl group containing 4 to 20 carbon atoms, an alkoxy group containing 1 to 20 carbon atoms, a fluorine atom, a chlorine atom or a bromine atom.

5. The silver halide color photographic material of claim 4, wherein $R_4$ represents an alkyl or alkoxy group substituted with at least one substituent selected from the group consisting of an aliphatic (including alicyclic) group, an aromatic group, a heterocyclic group, an aliphatic oxy group, an aromatic oxy group, an acyl group, an ester group, an amido group, a carbamoyl group, a sulfamoyl group, an imido group, a ureido group, an aliphatic or aromatic sulfonyl group, an aliphatic or an aromatic thio group, a hydroxyl group, a cyano group, a carboxyl group, a nitro group, a sulfo group and a halogen atom.

6. The silver halide color photographic material of claim 1, wherein L represents an alkylene group containing 1 to 20 carbon atoms in the main chain thereof.

7. The silver halide color photographic material of claim 6, wherein L represents an alkylene group substituted with at least one substituent selected from the group consisting of an aliphatic (including alicyclic) group, an aromatic group, a heterocyclic group, an aliphatic oxy group, an aromatic oxy group, an acyl group, an ester group, an amido group, a carbamoyl group, a sulfamoyl group an imido group, a ureido group, an aliphatic or aromatic sulfonyl group, an aliphatic or an aromatic thio group, a hydroxyl group, a cyano group, a carboxyl group, a nitro group, a sulfo group and a halogen atom.

8. The silver halide color photographic material of claim 1, wherein L represents an alkylene group represented by the formula

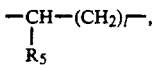

wherein $R_5$ represents a hydrogen atom, or a straight or branched chain alkyl group containing 1 to 30 carbon atoms, and l is an integer of from 0 to 10.

9. The silver halide color photographic material of claim 1, wherein m is 0 or 1.

10. The silver halide color photographic material of claim 1, wherein n is 1 or 2.

11. The silver halide color photographic material of claim 1, wherein X is a fluorine atom or a chlorine atom.

12. The silver halide color photographic material of claim 1, wherein the total number of carbon atoms in L and $(R_4)_n$ is 10 or above.

13. The silver halide color photographic material of claim 1, wherein the magenta coupler is contained in an amount of 0.1 to 1.0 mol per mol of silver halide in the emulsion layer.

* * * * *